United States Patent
de Koning et al.

(10) Patent No.: US 10,433,822 B2
(45) Date of Patent: Oct. 8, 2019

(54) SYSTEM AND METHOD FOR MEDICAL DIAGNOSTICS

(71) Applicant: Welch Allyn, Inc., Skaneateles Falls, NY (US)

(72) Inventors: Lezanne de Koning, Johannesburg (ZA); Robert L. Vivenzio, Auburn, NY (US); Raymond A. Lia, Auburn, NY (US); Tracy Bennett, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 562 days.

(21) Appl. No.: 15/136,226

(22) Filed: Apr. 22, 2016

(65) Prior Publication Data

US 2017/0303903 A1  Oct. 26, 2017

(51) Int. Cl.
| | |
|---|---|
| *A61B 10/02* | (2006.01) |
| *A61B 1/04* | (2006.01) |
| *A61B 1/303* | (2006.01) |
| *A61B 1/00* | (2006.01) |
| *A61B 1/05* | (2006.01) |

(52) U.S. Cl.
CPC ...... *A61B 10/0291* (2013.01); *A61B 1/00103* (2013.01); *A61B 1/00108* (2013.01); *A61B 1/00154* (2013.01); *A61B 1/05* (2013.01); *A61B 1/303* (2013.01); *A61B 2010/0216* (2013.01)

(58) Field of Classification Search
CPC ....... A61B 10/0291; A61B 1/04; A61B 1/303; A61B 2010/0216
See application file for complete search history.

(56) References Cited

U.S. PATENT DOCUMENTS

| | | | | |
|---|---|---|---|---|
| 4,784,158 A | * | 11/1988 | Okimoto | A61B 1/00142 600/572 |
| 4,788,985 A | | 12/1988 | Manning et al. | |
| 5,445,164 A | * | 8/1995 | Worthen | A61B 10/0045 600/572 |

(Continued)

OTHER PUBLICATIONS

Self Smear Test Kit to Perform Smear Test at Home; Hakan Gürsu; http://www.tuvie.com/self-smear-test-kit-to-perform-smear-test-at-home-by-hakan-gursu/; 6 pages.

(Continued)

*Primary Examiner* — Sean P Dougherty
*Assistant Examiner* — Nicholas E Kolderman
(74) *Attorney, Agent, or Firm* — Barclay Damon, LLP

(57) ABSTRACT

A system and a method for a medical diagnostic device are described herein. The medical diagnostic device can include an outer sleeve having a hollow interior and open distal and proximal ends, the outer sleeve being defined by a substantially tubular configuration including a proximal section having a substantially conical shape. A core is configured to be inserted axially within the outer sleeve. The core includes an axial inner cavity. The core is further defined by a proximal section having a conical shape substantially conforming to the proximal section of the outer sleeve. The core retains a diagnostic assembly, that can include at least one of a sample collecting assembly and an imaging assembly, that can be integrally or interchangeably attached and wherein the device can be utilized for self-patient or single patient use.

19 Claims, 31 Drawing Sheets

(56) References Cited

U.S. PATENT DOCUMENTS

| | | |
|---|---|---|
| 5,989,184 A | 11/1999 | Blair |
| 6,088,612 A | 7/2000 | Blair |
| 6,156,006 A | 12/2000 | Brosens et al. |
| 6,277,067 B1 | 8/2001 | Blair |
| 6,293,952 B1 | 9/2001 | Brosens et al. |
| 6,352,513 B1 | 3/2002 | Anderson et al. |
| 6,514,224 B1 * | 2/2003 | Anapliotis ............. A61B 10/00 206/209 |
| 6,712,761 B2 | 3/2004 | Borodulin et al. |
| 6,896,653 B1 | 5/2005 | Vail, III et al. |
| 6,926,677 B2 | 8/2005 | Richards |
| 8,679,013 B2 | 3/2014 | Ziarno et al. |
| 8,679,014 B2 | 3/2014 | Bennett et al. |
| 2002/0087096 A1 * | 7/2002 | Anderson .......... A61B 10/0045 600/572 |
| 2003/0225313 A1 | 12/2003 | Borodulin et al. |
| 2004/0068162 A1 | 4/2004 | Kirsner |
| 2005/0020937 A1 | 1/2005 | Reed et al. |
| 2005/0215858 A1 | 9/2005 | Vail, III |
| 2008/0188769 A1 | 8/2008 | Lu |
| 2009/0143646 A1 | 6/2009 | Vail, III |
| 2010/0016668 A1 | 1/2010 | Gal |
| 2011/0190579 A1 | 8/2011 | Ziarno et al. |
| 2011/0190581 A1 | 8/2011 | Bennett et al. |
| 2012/0157767 A1 | 6/2012 | Jendoubi |
| 2013/0211288 A1 * | 8/2013 | Zwart .................... A61B 10/02 600/569 |
| 2014/0088364 A1 | 3/2014 | Vail, III |
| 2014/0180165 A9 | 6/2014 | Zwart |
| 2014/0257098 A1 | 9/2014 | Del Priore |
| 2017/0042518 A1 * | 2/2017 | Sak .................... A61B 10/0291 |
| 2017/0319317 A1 * | 11/2017 | Biscay ................ A61D 19/027 |

OTHER PUBLICATIONS

Evalyn® Brush; Rovers Medical Devices; http://www.roversmedicaldevices.com/cell-sampling-devices/evalyn-brush/?lang=en; 3 pages.

* cited by examiner

SYSTEM AND METHOD FOR MEDICAL DIAGNOSTICS

TECHNICAL FIELD

This application generally relates to the field of medical devices and more specifically to a medical diagnostic device that permits various functionalities, such as imaging and sample collection that can be done interchangeably or in tandem. In at least one version, the medical diagnostic device can be used for body cavity examinations, such as examinations of the cervix.

BACKGROUND

There are known medical devices used for examining various anatomical cavities of patients. For example, vaginal specula are used in the diagnostic medical field to examine the cervix of a female patient. Over time, a number of various specula designs have been developed. Typically, a Graves speculum is defined by an upper blade and a lower blade, the latter including a pistol-grip like handle portion. The speculum is inserted in the vagina of a female patient and the upper and lower blades are articulated to facilitate examination of the cervix of the female patient.

After insertion of the vaginal specula, the medical professional can visually examine the patient's cervix, either by looking through the passage created between the blades of the vaginal speculum or by inserting an imaging device between the blades of the vaginal speculum. However, inserting the imaging device can disturb the inserted vaginal speculum and can be uncomfortable for the patient. Furthermore, the imaging device must be sterilized between uses to prevent any contamination from being transferred between patients. In addition to visually examining the patient's cervix, the medical professional can take a vaginal sample by inserting a sample collecting device within the passage created between the blades of the vaginal speculum and gathering the sample. The sample collecting device, however, may contact additional surfaces during the process, thus potentially contaminating the sample.

Vaginal specula require a clinician, or other caregiver, typically a medical professional, to insert the speculum and perform the examination. However, many patients experience embarrassment and discomfort at the idea of experiencing such an intimate and potentially uncomfortable examination. Because of this discomfort, many women elect not to have these examinations performed. As a result, serious medical conditions, such as cervical cancer, can remain undiagnosed or be diagnosed at a stage that is too late to effectively treat.

BRIEF DESCRIPTION

Various embodiments of a medical diagnostic device are described herein. Advantageously and according to at least one version, the medical diagnostic device can enable a patient to perform a self-examination and take patient samples without requiring the presence of a clinician. These samples and/or gathered image data can be sent to a medical professional for analysis and a follow-up office visit can be scheduled if the medical professional deems it appropriate.

In addition, embodiments of the medical diagnostic device described herein integrate sample and/or image collecting functions directly within the device. This integration simplifies operation of the device. Additionally, integration protects the sample collector from contamination during insertion and retraction of the medical diagnostic device.

According to a first aspect, a medical sampling device is described. The medical sampling device includes an outer sleeve having a hollow interior and open distal and proximal ends. The outer sleeve is defined by a substantially tubular configuration including a proximal section having a substantially conical shape. The medical sampling device also includes a core that is configured to be inserted axially within the hollow interior of the outer sleeve. The core can have a substantially tubular shape, including an axial inner cavity, and further including a proximal section having a conical shape substantially conforming to that of the proximal section of the outer sleeve. The medical sampling device can further include a sample collecting assembly. The sample collecting assembly includes a hollow rotatable shaft extending through the axial inner cavity of the core, the shaft having an engagement member positioned at a proximal end of the shaft and retained within the conical section of the core. The sample collecting assembly additionally includes an ejector pin extending entirely through the hollow rotatable shaft and a sample collector coupled to the ejector pin.

According to at least one version, the outer sleeve can further include a distal expansion section that is configured to transition between a closed position and an open deployed position. The distal expansion section can include a plurality of petals or fingers, the plurality of fingers being movable between the closed position and the open deployed position. The medical sampling device can further include a flexible sheath extending over the distal expansion section of the outer sleeve. The flexible sheath can be formed of an elastomeric material. According to at least one version, the proximal conical section of the outer sleeve can be compressible to enable the core and the sample collecting assembly to be retracted from a deployed position to an insertion position within the outer sleeve. The proximal conical section of the outer sleeve can include two or more locator pads positioned opposite each other to facilitate compression. The ejector pin is selectively engageable to eject the sample collector from the vaginal sampling device. The engagement member can be, for example, a rotatable knob that includes a recessed center portion sized to retain the ejector pin in a safety position in order to prevent unintentional ejection of the sample collector while in a deployed position within the patient. The sample collector includes a coupling portion configured to releasably couple the sample collector to a distal end of the ejector pin. For example, the coupling portion can include one of a keyway and a key and the distal end of the core or a rotatable shaft retaining the ejector pin can include the other of the keyway and the key to facilitate rotation of the sample collector. The sample collector can be a brush having a plurality of bristles that is supported for rotation to obtain a patient sample. The medical sampling device can further include an imaging device extending through the axial cavity of the core. A thin elastic sheath can be coupled to the outer sleeve. At least one stop surface can be positioned on an inner surface of the outer sleeve to prevent unintentional ejection of the core from the outer sleeve.

According to another aspect, a method for obtaining a sample from a patient using a medical diagnostic device is described herein. The diagnostic device includes an outer sleeve having a hollow interior with open distal and proximal ends, a core, and a sample collecting assembly. The sample collecting assembly includes a shaft having a sample collector at a distal end and an engagement member on an opposing proximal end. In this embodiment, the method includes inserting the sample collecting assembly axially through an inner cavity of a core, the core having a substantially tubular shape including a proximal section having a conical shape substantially conforming to a proximal section of the outer sleeve upon insertion. The method additionally includes inserting the core and sample collecting assembly axially through the outer sleeve and positioning the distal end of the vaginal diagnostic device within a vagina of the female patient. The method further includes repositioning the core and sample collecting assembly from an insertion position to a deployed position to extend the sample collector beyond the distal end of the outer sleeve and manipulating the sample collector to collect a patient sample, such as from the vagina or other anatomical cavity of a patient.

In an embodiment, the proximal section of the outer sleeve is compressible to enable the core and sample collecting assembly to be retracted from the deployed position to a nominal insertion position within the outer sleeve. The method can further include compressing the outer sleeve to retract the core and sample collecting assembly from the deployed position to the insertion position and withdrawing the medical diagnostic device from the patient. The method can further include engaging an ejector pin of the sample collecting assembly to eject the sample collector from the shaft. The sample collector can include a coupling portion configured to releasably couple the sample collector to a distal end of the shaft. According to at least one version, the coupling portion can include at least one keyway and at least one key and the distal end of the core or the shaft supporting the ejector pin can include the other of the keyway and the key to facilitate manipulation of the sample collector. Manipulation of the sample collector can include rotation of the sample collector.

The outer sleeve can further include a distal expansion section that is configured to transition between a closed position and an open deployed position. Repositioning the core and sample collection assembly can further include transitioning the distal expansion section from the closed position to the open deployed position to facilitate extending the sample collector and collecting the patient sample. The method can further include inserting an imaging device axially through the hollow rotatable shaft adjacent to the sample collector. The method can additionally include coupling a thin elastic sheath to the outer sleeve to provide stabilization, for example, in the instance of female patients who have had multiple children. A distal end of the outer sleeve can be inserted axially through a flexible sheath. The medical diagnostic device can be configured to be deployed within a body cavity (e.g., the vagina) of a patient and to be acted upon to collect a sample.

According to yet another aspect, a medical diagnostic device is described. The medical diagnostic device includes an outer sleeve having a hollow interior and open distal and proximal ends. The outer sleeve is defined by a substantially tubular configuration including a proximal section having a conical shape. The medical diagnostic device also includes a core configured to be inserted axially within the outer sleeve. The core has a substantially tubular shape including an axial cavity and a proximal section having a conical shape substantially conforming to the proximal section of the outer sleeve. The core further includes a diagnostic assembly retained therein.

In at least one embodiment, the diagnostic assembly can be a sample collecting assembly. The sample collecting assembly can include a hollow rotatable shaft extending through the axial cavity of the core, the shaft having an engagement member positioned at a proximal end of the shaft and retained within the conical section of the core, an ejector pin extending entirely through the hollow rotatable shaft, and a sample collector coupled to the ejector pin. In another embodiment, the diagnostic assembly can include an imaging device, such as a borescope, positioned in a sampling end of the axial cavity of the core. A cable can extend through the axial cavity of the core to couple the imaging device to an external computing device. In yet another embodiment, the diagnostic assembly includes a hollow rotatable shaft extending through the axial cavity of the core, the shaft having an engagement member positioned at a proximal end of the shaft and retained within the conical section of the core, an ejector pin extending entirely through the hollow rotatable shaft, a sample collector coupled to the ejector pin, and an imaging device positioned adjacent to the sample collector. The medical diagnostic device can further include a distal expansion section of the outer sleeve configured to transition between an unopened insertion position and an open deployed position. A flexible sheath can extend over the expansion section of the outer sleeve.

By having an imager in the core in addition to a sampling device, a user can more efficiently direct the sampling device to the intended target of interest. Photographs or streaming video can be taken of the intended target of interest to document abnormalities for contemporaneous or later examination by a clinician. Additionally, the images or video can be stored for future reference or training purposes. This imaging will also allow the patient to see images of the target of interest directly and in which the photographs or video can be sent to the clinician or elsewhere for archiving.

These and other features and advantages will become apparent to those skilled in the art when taken with reference to the following more detailed description of the various embodiments of the invention in conjunction with the accompanying drawings that are first briefly described.

BRIEF DESCRIPTION OF THE DRAWINGS

The accompanying drawings, which are incorporated herein and constitute part of this specification, illustrate presently various embodiments of the invention, and, together with the general description given above and the detailed description given below, serve to explain features of the invention (wherein like numerals represent like elements) in which.

DETAILED DESCRIPTION

Figure 1:
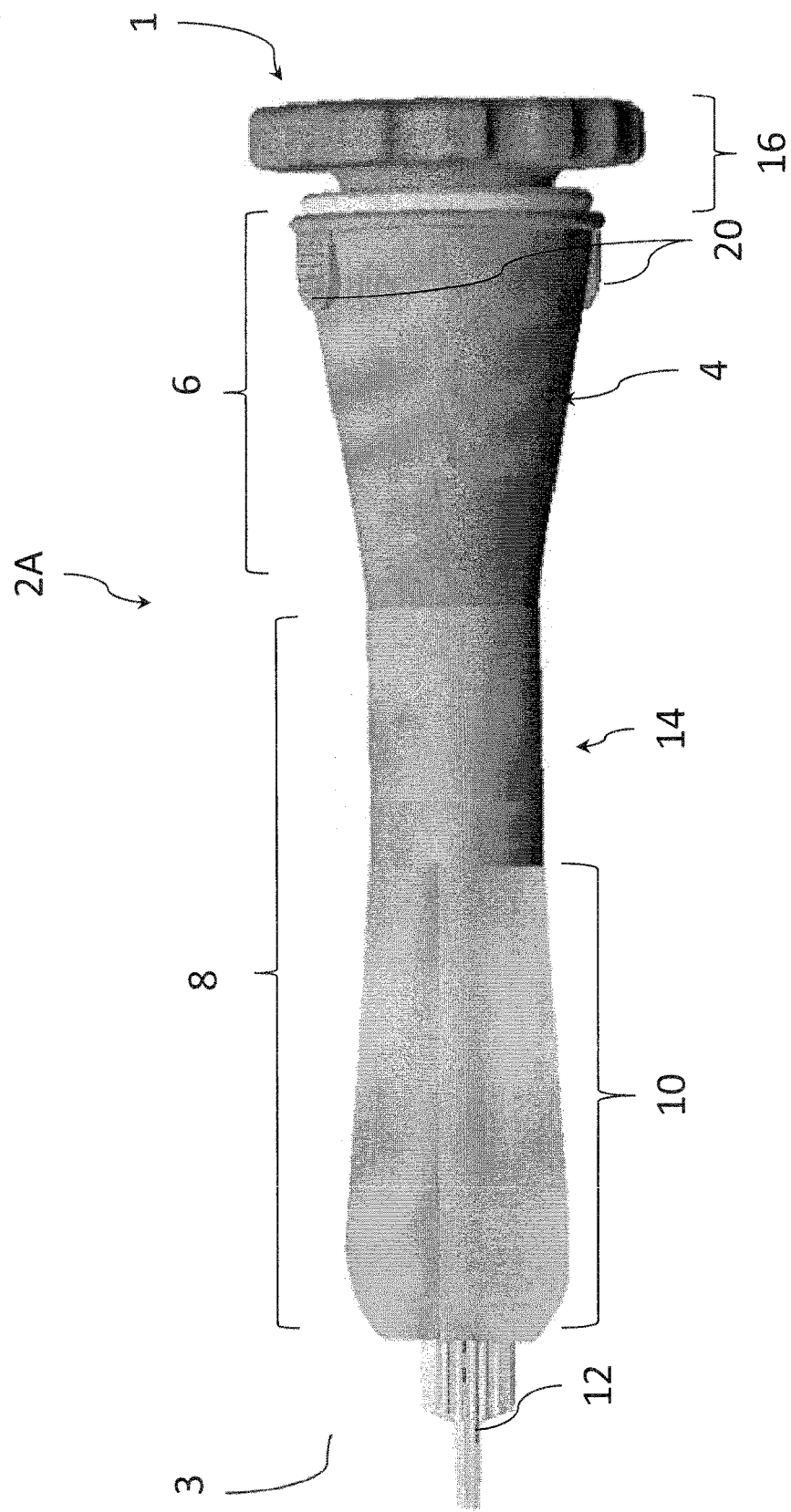
FIG. 1 illustrates a side elevational view of a medical diagnostic device in accordance with an embodiment, the diagnostic device being shown in a deployed position.

The following Detailed Description should be read with reference to the accompanying drawings, in which like elements in different drawings are identically numbered for the sake of clarity. The drawings, which are not necessarily to scale, are intended to depict salient features of the design in selected embodiments and are not intended to limit the intended scope of the invention, except where so expressly indicated. The Detailed Description illustrates by way of example, not by way of limitation, the principles of the invention. This Description will clearly enable one skilled in the art to make and use the invention, and describes several embodiments, adaptations, variations, alternatives and uses of the invention, including what is presently believed to be the best mode of carrying out the invention.

In addition, various terms are used throughout in order to provide a suitable frame of reference with regard to the accompanying drawings such as "lower", "upper", "top", "within", "lateral", "upon", "front", "back", and the like. These terms are also not intended to overly limit the scope of the herein described invention. As used herein, the terms "patient" or "user" refer to any human or animal subject such as a clinician or other caregiver, and are not intended to limit the systems or methods to human use, although use of the subject invention in a human patient represents a preferred embodiment. As used herein, the term "distal end" refers to an end of the herein described diagnostic device closest to the patient during use, and the term "proximal end" refers to an end of the herein described medical diagnostic device furthest from the patient during use.

The terms "about" and "substantially" are used in connection with a numerical value throughout the description and claims denotes an interval of accuracy, familiar and acceptable to a person skilled in the art. The interval governing this term is preferably ±30%. Unless specified, the terms described above are not intended to narrow the scope of the invention as described herein and according to the claims.

Certain embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting and that the scope of the present disclosure is defined solely by the claims. For purposes of the following description, it should further be noted that the features illustrated or described in connection with one embodiment may be combined with the features of other embodiments. Such modifications and variations are intended to be included within the intended scope of the present disclosure. For purposes of the following embodiments, the devices that are described herein are intended for use in conducting vaginal examinations. It will be readily understood, however, that similar devices having features as described herein can also be used in connection with the examination of other anatomical cavities of a patient.

With reference to the drawings and according to FIGS. 1-6B, there is depicted a medical diagnostic device 2A in accordance with a first embodiment. In this particular embodiment, the medical diagnostic device 2A is a vaginal sampling device that is defined by respective open proximal and distal ends 1, 3 and in which the distal end 3 of the device 2A is also synonymously referred to herein as a "sampling end". The medical diagnostic device 2A includes an outer sleeve 4 that is defined by a substantially tubular configuration and a hollow interior 9. According to this specific embodiment, the outer sleeve 4 is further defined by a proximal section 6 having a substantially conical shape and an opposing distal section 8. In accordance with this embodiment, the substantially conical proximal section 6 of the hollow outer sleeve 4 (or the entire outer sleeve) is made from a lightweight plastic or other suitable material that enables the substantially conical proximal section 6 to be flexed (i.e., compressed) inwardly. To facilitate this compression, the substantially conical proximal section 6 of the outer sleeve 4 can include at least two locator pads 20, each positioned diametrically opposite each other to identify where to apply pressure to the conical proximal section 6.

The distal section 8 of the outer sleeve 4 includes an expansion section 10 that is configured to expand and retract. In an example, the expansion section 10 may be formed of a plurality of fingers 11 that are configured to move toward and away from each other as the expansion section 10 expands and retracts. More specifically and according to this particular embodiment, the fingers 11 are circumferentially disposed and defined by a series of axial cuts 13, FIG. 4B, that are formed in the outer sleeve 4 and extending from the distal end of the sleeve 4 toward the proximal end thereof.

In accordance with this specific embodiment, an elastically deformable sheath 14 overlays the distal section 8 of the outer sleeve 4, including the expansion section 10 of the device 2A, such that the elastically deformable sheath 14 substantially covers the tubular section of the outer sleeve 4. In an example, the elastically deformable sheath 14 can be formed of an elastomeric material or a rubber-like material in which the shape of the sheath 14 is created by injection or blow molding or by another suitable manufacturing process. When attached in overlaying fashion to the outer sleeve 4, the sheath 14 elastically deforms or stretches as the expansion section 10 expands and similarly contracts as the expansion section 10 contracts. Functionally, the elastically deformable sheath 14 acts to prevent the expansion section 10 from pinching the patient when in use.

In addition, a core 16 is sized and configured to be retained axially within the hollow interior 9 of the outer sleeve 4. According to this specific embodiment, the core 16 is defined by a substantially tubular shape having a distal section 27, as well as an opposing proximal section 28, wherein the latter proximal section 28 is further defined by a substantially conical shape that closely corresponds with that of the substantially conical proximal section 6 of the outer sleeve 4. At least one stop surface 38 can be positioned along the inner surface of the outer sleeve 4. According to this embodiment, the at least one stop surface 38 interacts with at least one stop groove 40, formed on an exterior surface of the core 16 to prevent the core 16 from falling out of the outer sleeve 4 when the vaginal diagnostic device 2A is inserted in the female patient.

Figure 2:
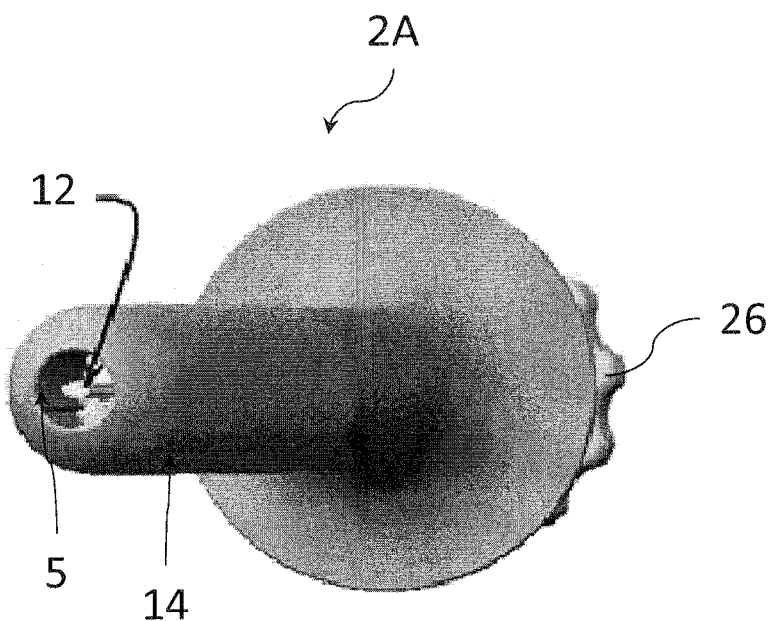
FIG. 2 illustrates a front perspective view of a medical diagnostic device in accordance with an embodiment and in an insertion position.
Figure 3:
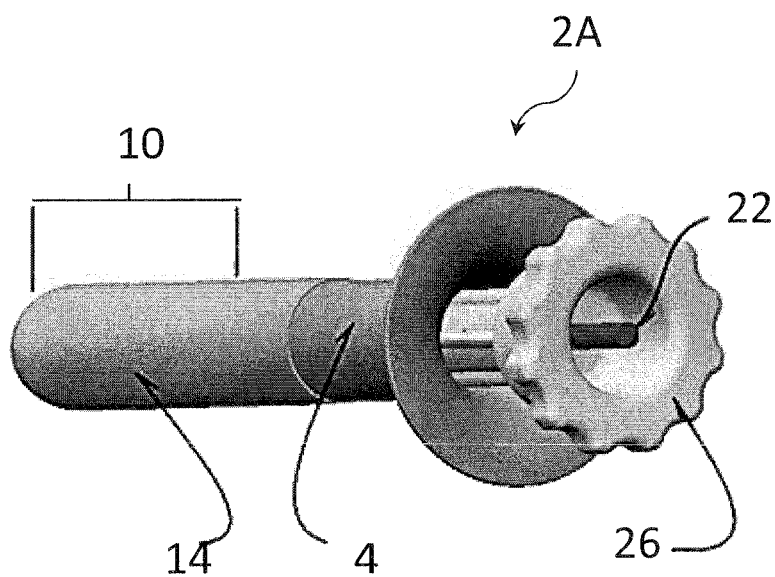
FIG. 3 illustrates a rear perspective view of the medical diagnostic device of FIG. 2.
Figure 4A:
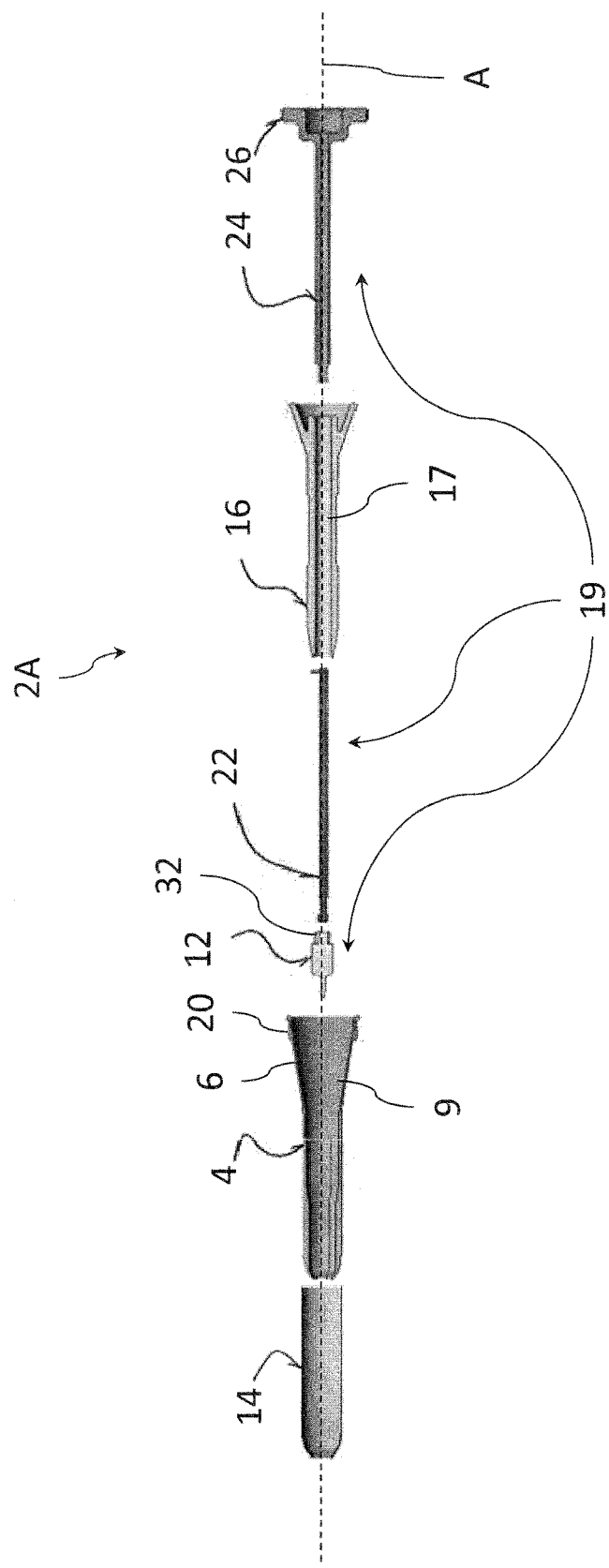
FIG. 4A illustrates an exploded assembly view of the medical diagnostic device of FIGS. 1-3.
Figure 4B:
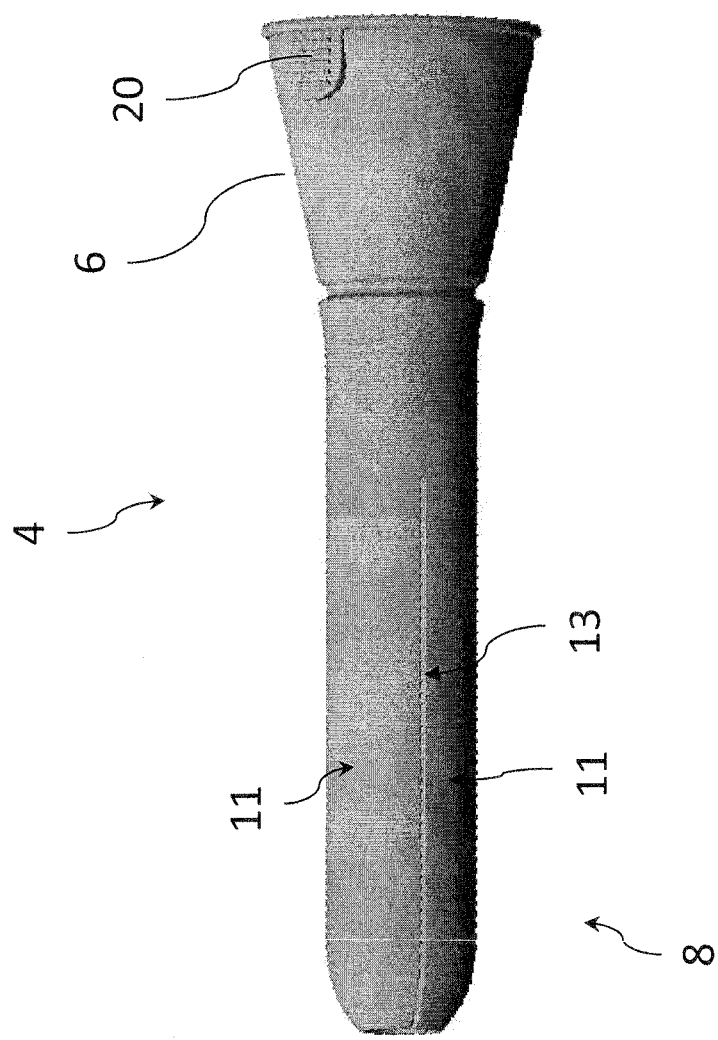
FIG. 4B is a side elevational view of the outer sleeve of the diagnostic device of FIG. 4A.

Still referring to FIGS. 1-6B, the core 16 is defined by an axial cavity 17 extending through the length of the core 16 along an axis A, FIG. 4. The axial cavity 17 is configured to retain a diagnostic assembly therein. According to this specific embodiment, the diagnostic assembly is a sample collecting assembly 19 that is defined by a sample collector 12, an ejector pin 22, and a hollow rotatable shaft 24. In the illustrated embodiment, the hollow rotatable shaft 24 has an engagement member 26 positioned at a proximal end 18 of the rotatable shaft 24 and the core 16. The engagement member 26 is retained within the conical proximal section 28 of the core 16 when the sample collecting assembly 19 is retained in the core 16. The ejector pin 22 is inserted axially within and extends entirely through the hollow rotatable shaft 24. The engagement member 26 facilitates manipulation, such as rotation about axis A, of the hollow rotatable shaft 24, the ejector pin 22, and the sample collector 12.

Figure 6A:
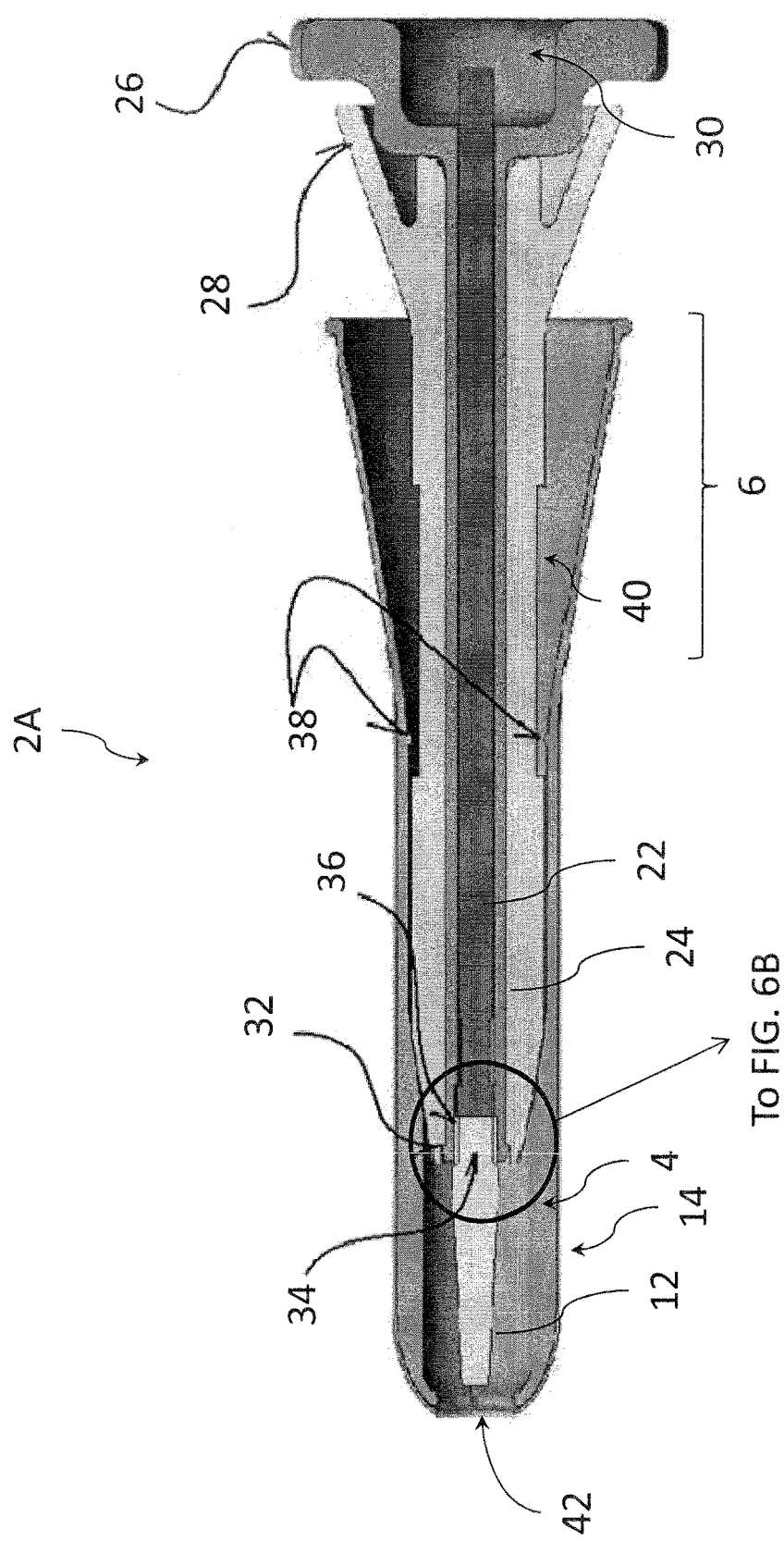
FIG. 6A illustrates another side elevational view, taken in section, of the medical diagnostic device shown in an insertion position.
Figure 6B:
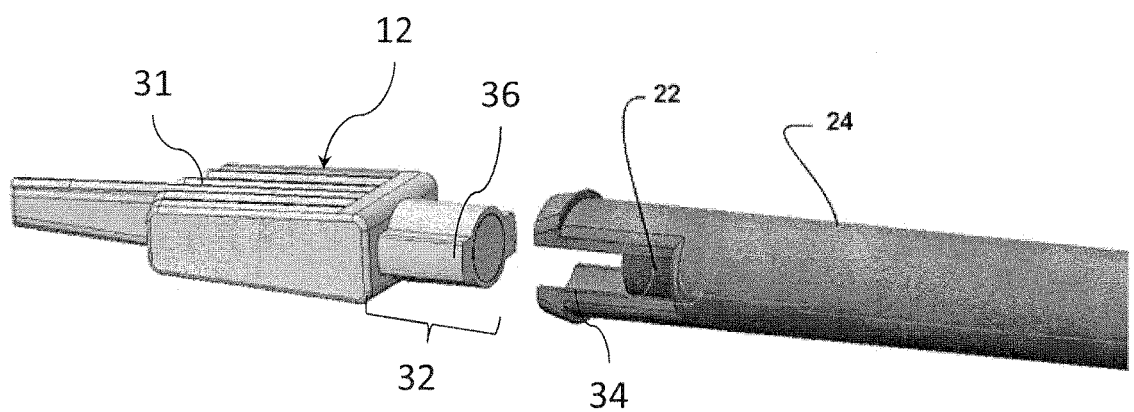
FIG. 6B is a partial side perspective view of the medical sampling device of FIG. 6A, showing as exploded, a sample collector, the ejector pin, and the end of the hollow rotatable shaft, and showing connection features between same.

The sample collector 12 is coupled to the ejector pin 22 and the hollow rotatable shaft 24 at the distal end 3 of the device 2A. The sample collector 12 can be any suitable device for collecting a vaginal sample, such as a brush having a plurality of disposed bristles 31. The sample collector 12 can have a coupling portion 32 that is configured to releasably couple the sample collector 12 relative to a distal end of the rotatable shaft 24. As illustrated by FIG. 6B, the coupling portion 32 is one of a keyway and a corresponding key formed at the proximal end of the sample collector 12 and the distal end of the rotatable shaft 24 including the other of the keyway and the corresponding key. For example and as shown according to this embodiment, a set of female keyways 34 are formed at the distal end of the hollow rotatable shaft 24 that receives a corresponding set of keys 36 formed on the proximal end (coupling portion 32) of the sample collector 12. Ejection is permitted when the ejector pin 22 is axially advanced toward the distal end of the device 2A, which corresponding advances the sampling collector 12 and more specifically the keys 36 from the keyways 34. Other suitable releasable connections can be utilized, provided that these components remain coupled until ejection or removal of the sampling collector 12 is desired. This coupling portion 32 facilitates rotation of the sample collector 12 using the hollow rotatable shaft 24 during collection of a patient sample.

Figure 8:
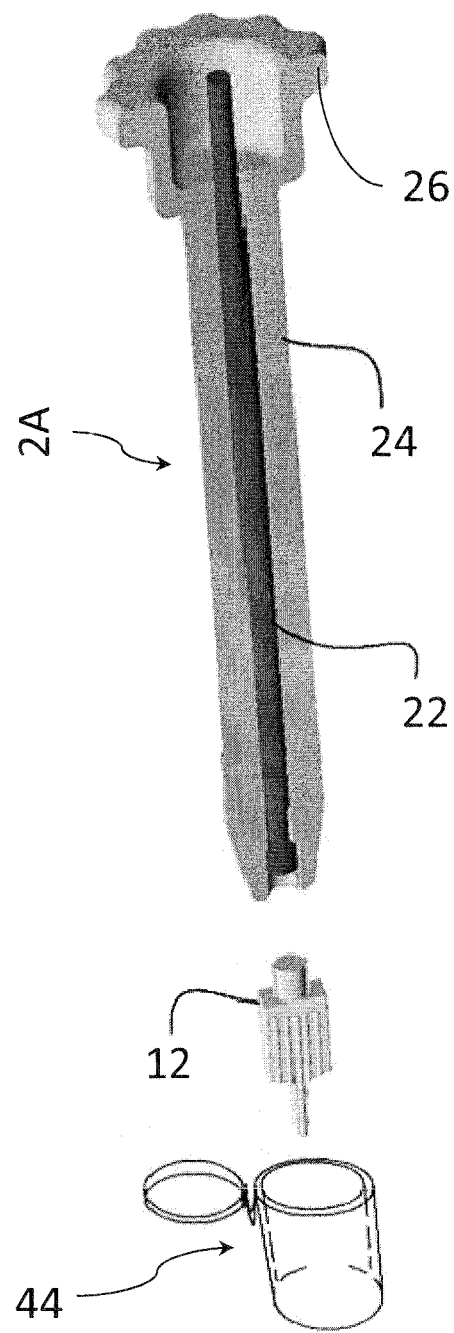
FIG. 8 illustrates a partial perspective view of the medical diagnostic device of FIGS. 6A-7, depicting the ejection of a sample collector.

According to this embodiment, the ejector pin 22 is selectively engageable to eject the sample collector 12 from the medical diagnostic device 2A. As illustrated herein, the engagement member 26 includes a recessed center portion 30 that is sized to retain the ejector pin 22 in a "safety" position in order to prevent unintentional ejection of the sample collector 12 via the ejector pin 22. For example, this safety position prevents ejection of the sample collector 12 from the ejector pin 22 while the medical diagnostic device 2A is inserted in a female patient. As illustrated in FIG. 8 and when the ejector pin 22 is engaged, the sample collector 12 is released from the sample collecting assembly 19. In an example, the sample collector 12 can be released from the assembly for depositing into a sample container 44. This sample container 44 can be then be transported to a medical practitioner or a laboratory for testing.

Figure 9:
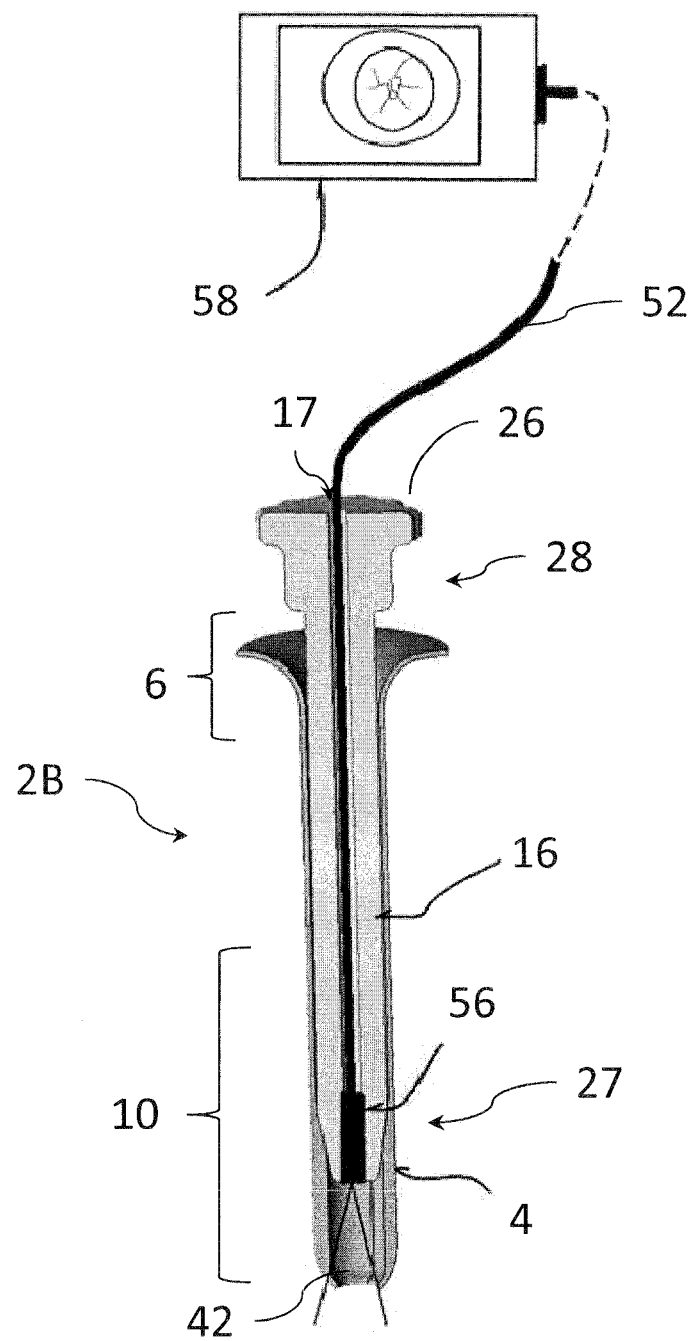
FIG. 9 illustrates a sectioned view of a medical diagnostic device in accordance with another embodiment, including an imaging device.

Another embodiment of a medical diagnostic device 2B is illustrated in FIG. 9. As in the prior embodiment, the vaginal diagnostic device 2B according to this version also includes an outer sleeve 4 having a substantially tubular configuration including a substantially conical proximal section 6 as well as an opposing distal section. In addition, a core 16 is also similarly retained axially within the hollow interior 9 of the outer sleeve 4 in which the core 16 is defined by respective distal and proximal sections 27, 28 and further includes an inner axial cavity 17 extending axially through the distal and proximal sections 27, 28. In this embodiment, the core 16 has an engagement member 26 coupled to the proximal section 28 of the core 16. In this version, the proximal section 28 of the core 16 is not conical in configuration though the latter section 28 is still sized and configured to engage the conical proximal section 6 of the outer sleeve 4. As discussed above, the core 16 is configured to retain a diagnostic assembly within the axial cavity 17. According to this embodiment, the diagnostic assembly is an imaging device 56 that is inserted axially within the inner axial cavity 17 of the core 16 and positioned within the distal section 27. The imaging device 56 may, for example, be a CCD, CMOS, ultrasound, infrared, RF, or other form of electronic device. According to this version, the imaging device 56 is a borescope having an electronic imager having a cover glass to protect the interior of the imager from contaminants and an imaging lens disposed within a compact housing that is tethered to a power source (not shown) such as an AC power supply or, alternatively, to batteries or other compact and portable power supply, such as a super capacitor (not shown). The imaging device 56 can include at least one LED or other illumination source disposed in relation to the electronic imager to provide sufficient illumination of the medical target of interest (e.g., the vagina). The imaging device 56 can be configured to gather still images, video, or both still images and video, which can be displayed to the caregiver or the patient on a computer, tablet, pad or mobile device.

According to this embodiment, the outer sleeve 4, and more specifically the distal section of the vaginal diagnostic device 2B, has an expansion section 10. When the core 16 advances within the outer sleeve 4, the expansion section 10 is configured to expand from a closed position upon insertion to an open or deployed position and wherein the expansion section 10 can include a series of circumferentially spaced fingers 11, FIG. 7, that are expanded outwardly radially when in the deployed position. The axial advancement of the core 16 relative to the target of interest positions the imaging device 56 closer to the opening 42 of the distal end of the outer sleeve 4, thereby improving the visual coverage of the imaging device 56 and resulting in a "zoom" effect.

In accordance with an embodiment, the imaging device 56 can be coupled to a computing device 58 to which gathered image data can be transmitted for analysis. The computing device 58 can be any suitable device, such as a computer, a tablet, or a smartphone, among others. While the imaging device 56 is illustrated here as being coupled to the computing device 58 via a wired connection 52, it is to be understood that the imaging device 56 may alternatively be wirelessly coupled to the computing device 58. In an example, the image data can be transmitted to a patient's computing device 58 and the patient can transmit the data from the computing device 58 to a medical professional for analysis, such as through a medical data network. In another example, the image data can be transmitted directly from the imaging device 56 to a medical professional's computing device 58.

Figure 10A:
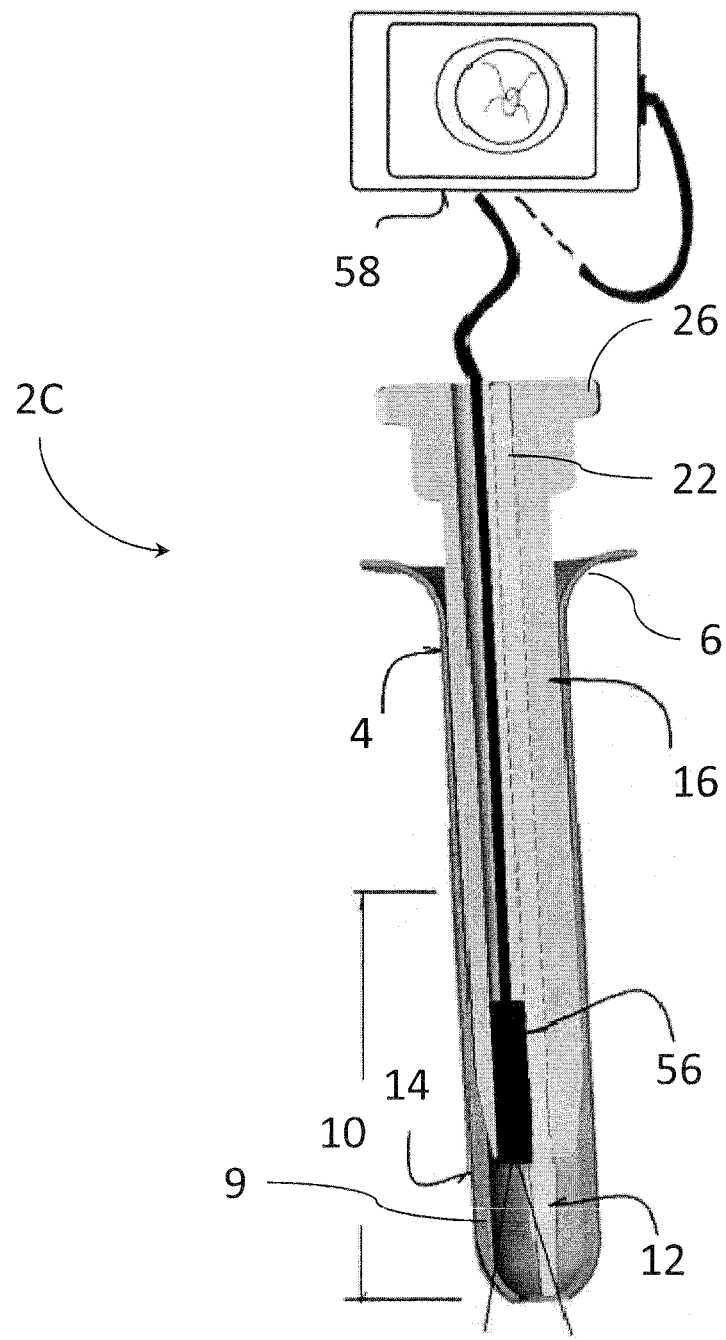
FIG. 10A illustrates a sectioned view of a medical diagnostic device in accordance with another embodiment, including an imaging device and a sample collector.
Figure 10B:
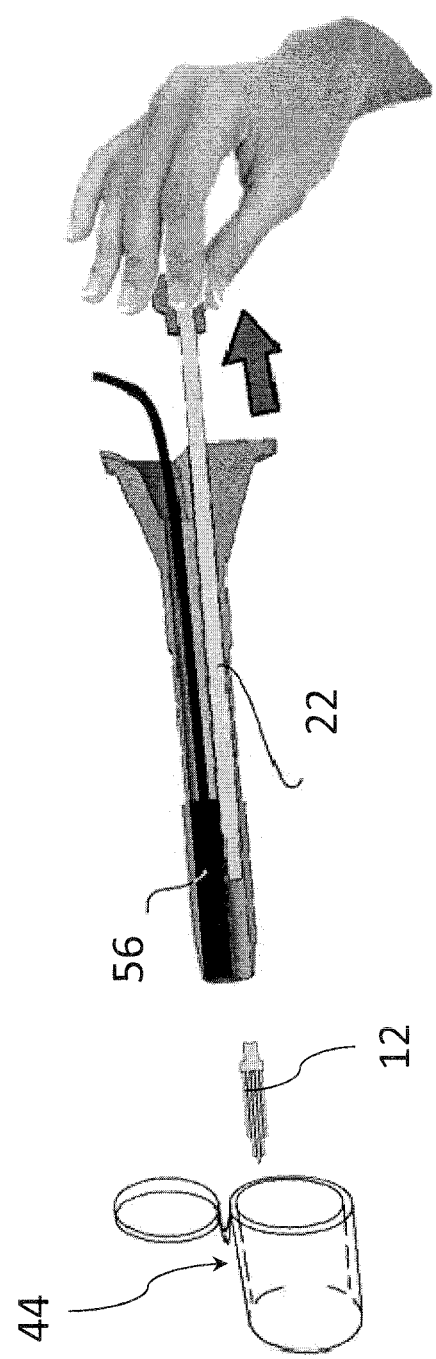
FIG. 10B illustrates a sectioned view of the medical diagnostic device of FIG. 10, depicting the ejection of the sampling device.

With reference to FIGS. 10A and 10B, there is depicted another embodiment of a medical diagnostic device 2C. Similarly to the prior embodiments discussed herein, the vaginal diagnostic device 2C includes an outer sleeve 4 having a tubular configuration with a proximal conical portion 6 and in which the outer sleeve 4 is further defined by a hollow interior 9. The outer sleeve 4 also has a distal expansion section 10 that can be overlaid by an elastically deformable sheath 14. A core 16 is disposed axially within the hollow interior 9 of the outer sleeve 4 and includes an engagement member 26 coupled to a proximal section 28 of the core 16, the latter section 28 being fitted within the substantially conical proximal portion 6 of the outer sleeve 4. In this specific embodiment, the diagnostic assembly includes a vaginal sampling assembly 19 as well as an imaging device 56. The vaginal sampling assembly 19 includes an ejector pin 22 disposed axially through the interior of the core 16 and a sample collector 12 that is releasably coupled to the ejector pin 22. The imaging device 56 is also disposed axially through the interior of the core 16 and is positioned adjacent to the sample collector 12 in substantially parallel relation. As in the preceding, the imaging device 56 can be a borescope that is coupled to a computing device 58 by means of a wired or wireless connection to transmit image data that is gathered by the imaging device 56 to the computing device 58 for display and archiving. According to this specific embodiment, the sampling and imaging components are disposed in parallel relation to one another and off center within the apparatus (core 16).

During use, the medical diagnostic device 2C is inserted within an anatomical body cavity (e.g., the vagina) of the patient and the core 16 is advanced toward the distal end within the outer sleeve 4. Upon axial advancement of the core 16, the expansion section 10 is configured to have its fingers 11, FIG. 7, expand outwardly radially with the imaging device 56 and the sample collector 12 advancing toward the distal end of the diagnostic device 2C to collect image data and vaginal samples, respectively.

Figure 5:
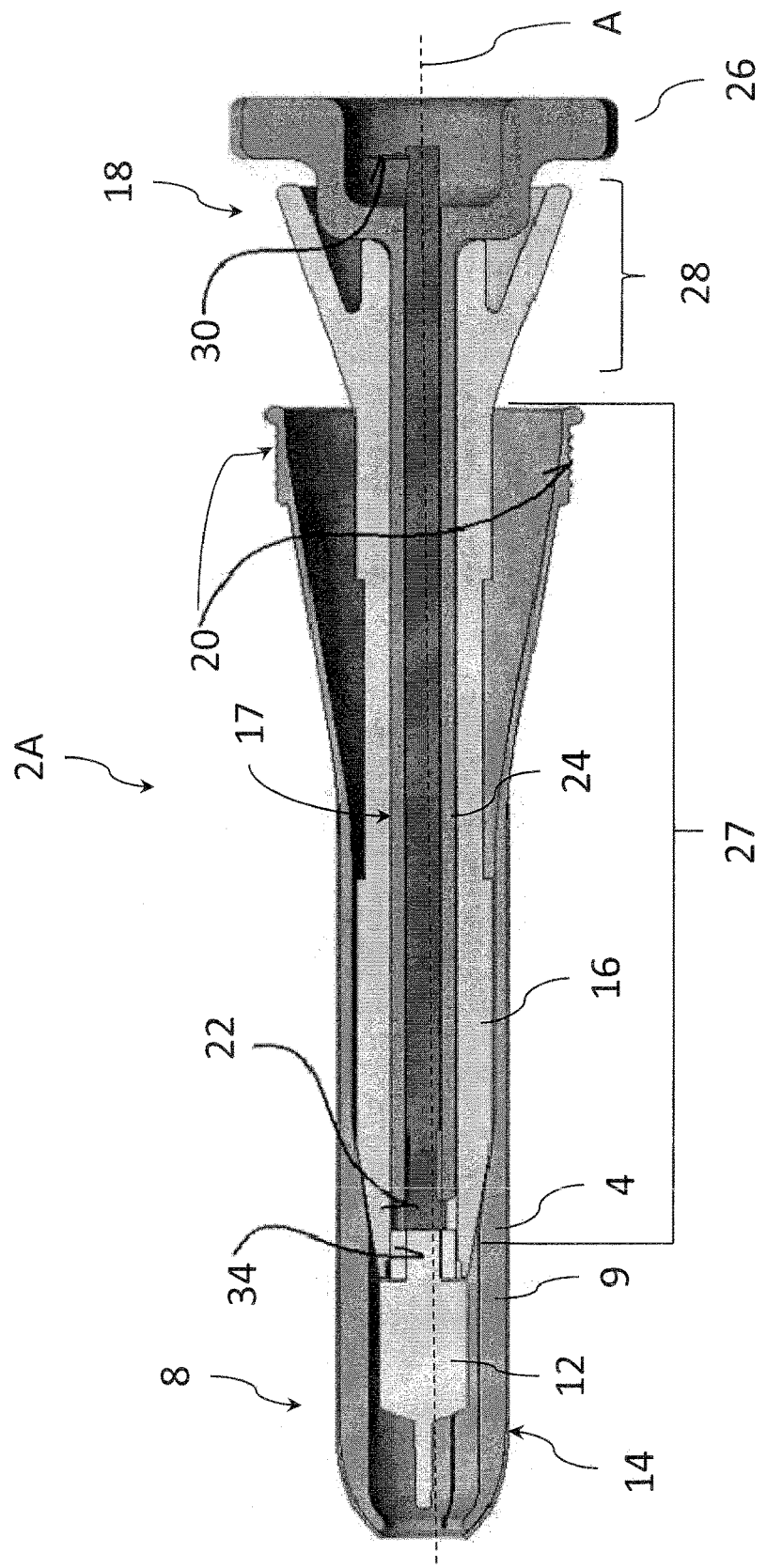
FIG. 5 illustrates the side elevational view of the medical diagnostic device of FIGS. 1-4B, taken in section and in which the diagnostic device is shown in the insertion position.
Figure 7:
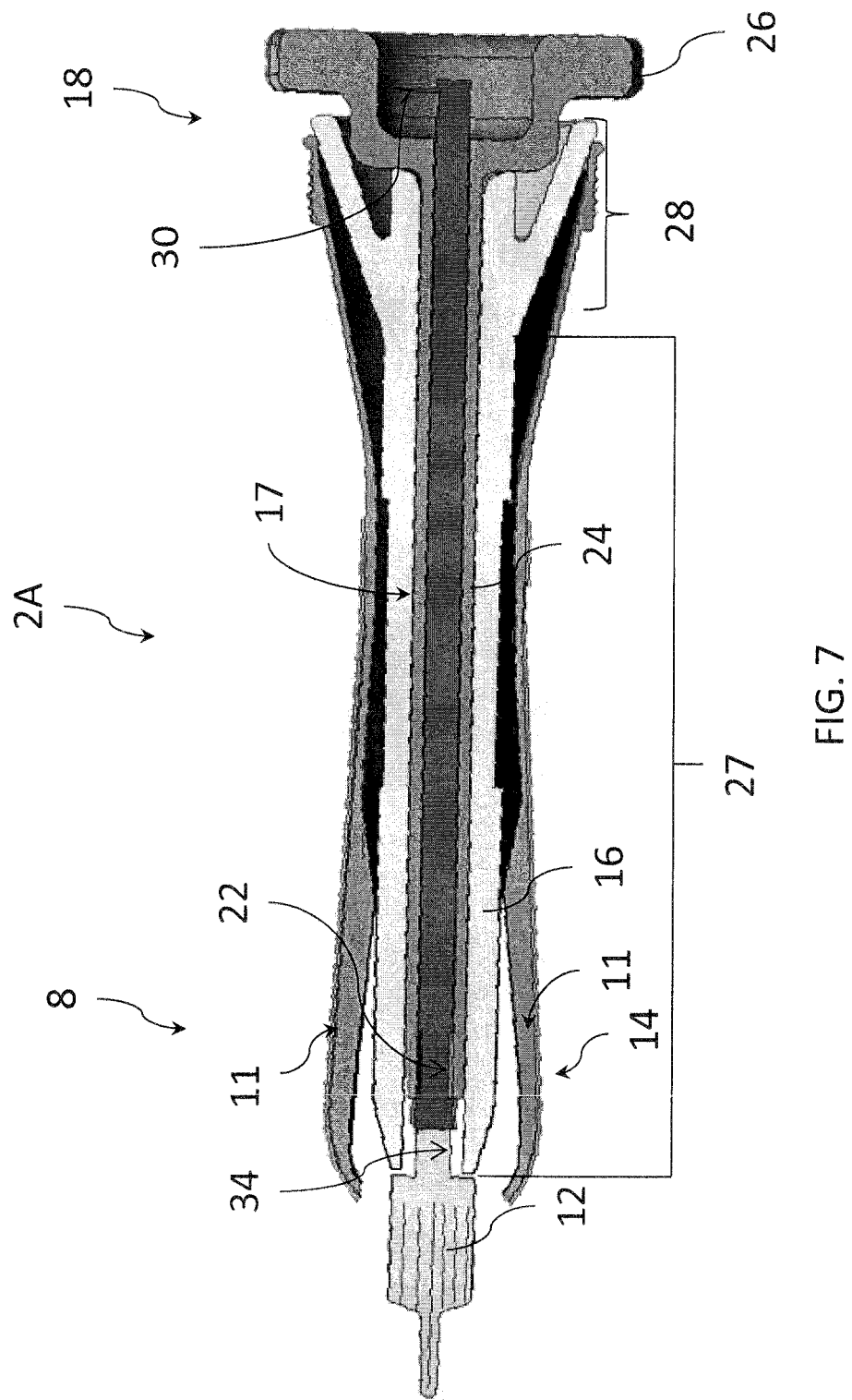
FIG. 7 illustrates a side elevational view of a medical diagnostic device, shown in section, and depicting a sample collecting assembly in a deployed position.

As discussed above, each of the previously described medical diagnostic devices 2A, 2B, 2C commonly includes a distal expansion section 10 that is configured to transition between a closed insertion position and an open or deployed position. As illustrated in FIGS. 5-6 and when the medical diagnostic device 2A, 2B, 2C is inserted into the anatomical cavity of the patient, the expansion section 10 is initially in a closed, non-expanded position, the sample collector 12 is positioned within the outer sleeve 4, and the core 16 is not advanced within the outer sleeve 4 so that the substantially conical proximal section 28 of the core 16 is not received in the hollow conical section 6 of the outer sleeve 4. As illustrated in FIG. 7 and when the medical diagnostic device 2A, 2B, 2C is in the open, deployed position, the expansion section 10 expands, the sample collector 12 extends beyond the outer sleeve 4 through an opening 42 in the outer sleeve 4, and the core 16 advances axially within the outer sleeve 4 toward the distal end so that the conical section 6 of the outer sleeve 4 receives the conical section 28 of the core 16. When the conical section 6 of the outer sleeve 4 is compressed, using the at least two locator pads 20, FIG. 1, or otherwise, the medical diagnostic device 2A, 2B, 2C transitions back from the deployed position to the insertion position. During this transition, the at least one stop surface 38 of the outer sleeve 4 interacts with the at least one stop groove 40 on the outer surface of the core 16 to prevent the core 16 from falling out of the outer sleeve 4 when the medical diagnostic device 2A, 2B, 2C is inserted in the female patient. This stop surface 38 and stop groove 40 are particularly efficacious for preventing the core 16 from falling out of the outer sleeve 4 when the medical diagnostic device 2A, 2B, 2C transitions from the deployed position to the insertion position.

As discussed, the herein depicted diagnostic device 2A, 2B, 2C is capable of assuming various positions when used in conjunction with a patient. More specifically and according to this depicted embodiment and when the medical diagnostic device 2A, 2B, 2C is in the open or "deployed" position, as illustrated in FIG. 1, the expansion section 10 is caused to expand, allowing a diagnostic device, such as a sample collector 12 or imaging device 56, to extend from the interior of the outer sleeve 4. As will be further discussed below, the core 16 is configured to axially advance within the outer sleeve 4. Advancement of the core 16 within the outer sleeve 4 extends the sample collector 12 beyond the outer sleeve 4 as the expansion section 10 outwardly and radially expands from the insertion position to the deployed position.

When the medical diagnostic device 2A, 2B, 2C is in the closed insertion position, as illustrated in FIGS. 2-3, the expansion section 10 is not yet expanded, facilitating insertion of the medical diagnostic device 2 into the body cavity, such as the vagina of a female patient. In this closed insertion position, the diagnostic device, (e.g., the sample collector 12 or imaging device 56) remains retracted within the hollow interior 9 of the outer sleeve 4. This retracted position of the sample collector 12 facilitates insertion of the medical diagnostic device 2 and protects the sample collector 12 from inadvertently touching vaginal tissue until the diagnostic device 2A, 2B, 2C is properly positioned.

As discussed above, the substantially conical proximal section 6 of the outer sleeve 4 can be flexed or compressed inwardly. In particular, during use, a inwardly radially directed force is applied simultaneously to the exterior of the proximal section 6 and preferably to the at least two locator pads 20, FIG. 1, causing inward flexion of the conical proximal section 6 towards the axis A. This inward flexion causes corresponding portions of an internal wall surface of the proximal section 6 to be placed into intimate contact with an outer or external surface of the substantially conical proximal section 28 of the core 16. This engagement triggers axial retraction of the core 16 and the sample collector 12 along the axis A (FIG. 5) from the open deployed position in which the core 16 is advanced within the outer sleeve 4 and the sample collector 12 extends beyond the outer sleeve 4 to the closed insertion position in which the core 16 and the sample collector 12 are retracted within the hollow interior 9 of the outer sleeve 4.

As discussed above, in an embodiment, the expansion section 10 may be formed of a plurality of fingers 11 which are positioned adjacent to each other when the medical diagnostic device 2A, 2B, 2C is in the closed insertion position. When the medical diagnostic device 2A, 2B, 2C is in the deployed position, the spacing between the fingers 11 increases in order to expand the expansion section 10. For example, as the core 16 advances axially along the outer sleeve 4, the core 16 pushes against the fingers 11, causing the fingers 11 to move radially outwardly, away from each other. In this example, the elastically deformable sheath 14 prevents the flesh of the patient from becoming caught and pinched between the moving fingers 11. An inflatable cuff (not illustrated) can additionally be pneumatically and mechanically coupled to the hollow outer sleeve 4 to provide additional support and stabilization for the vaginal tissue of the patient. In one version, the inflatable cuff could be used in lieu of the fingers.

A method of employing a medical diagnostic device 2, in accordance with an embodiment, is herein sequentially illustrated in FIGS. 11A-11H. The medical diagnostic device 2, which in this specific instance is most closely similar to the device 2A, can be employed to examine the vagina of a female patient 80, although any of the herein described devices or equivalents could be similarly employed. In an embodiment, the medical diagnostic device 2 described herein can be used by a patient to perform an self-diagnosis without the need for a medical professional to be physically present during the examination. In an example, the examination can be performed by the female patient 80 in the patient's home or in private in a medical office. In another embodiment, the medical diagnostic device 2 can be employed by a medical professional in performing an examination of the female patient 80.

Figure 11A:
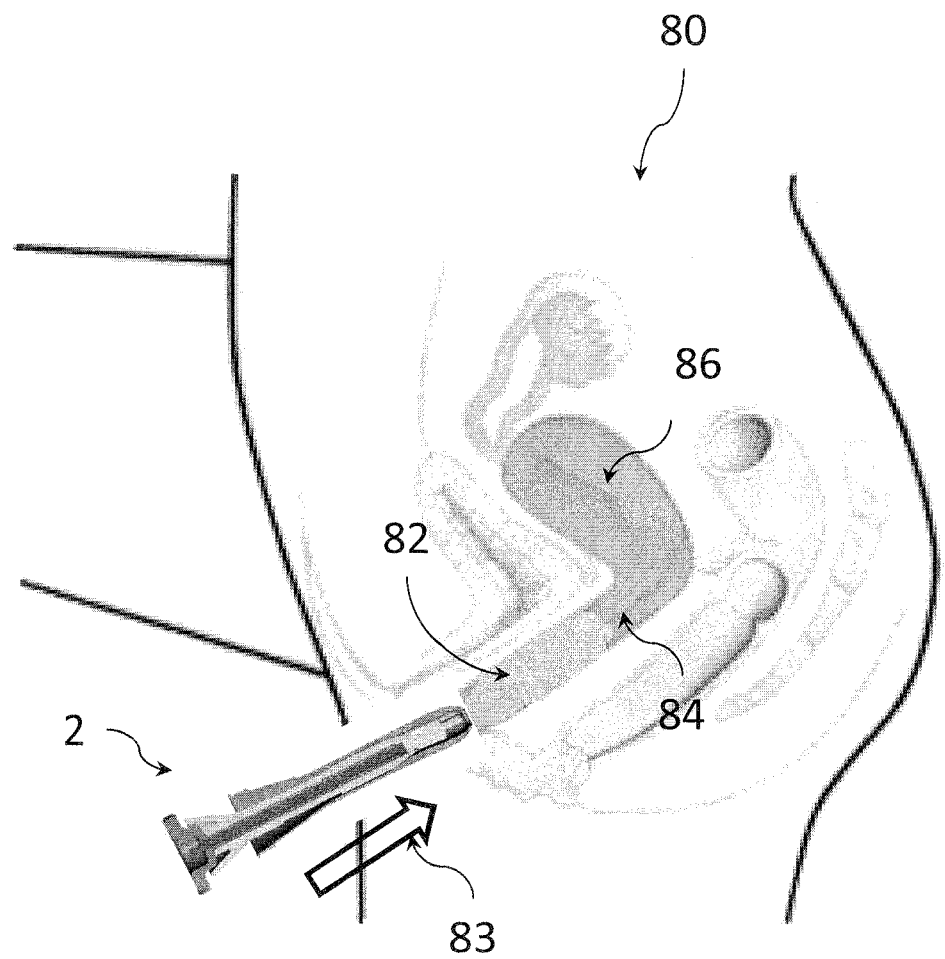
FIGS. 11A-11H are sequential views, taken in section, of a method of using a medical diagnostic device in accordance with an embodiment.
Figure 11B:
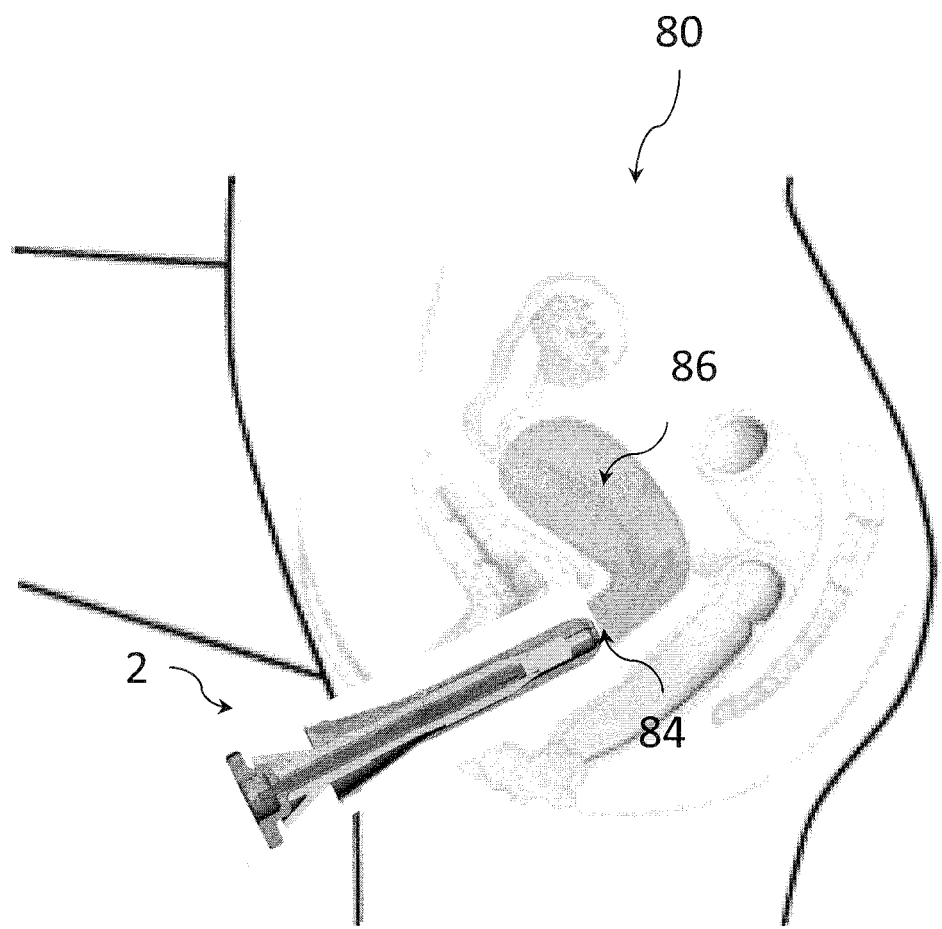

Initially and as illustrated in FIG. 11A and during an examination, the distal end of the medical diagnostic device 2 is inserted in the vagina 82 of the female patient 80 and advanced in the direction depicted by arrow 83, within the vagina 82 toward the cervix 84. When the distal end of the vaginal diagnostic device is positioned near the cervix 84 and before the uterus 86, as illustrated in FIG. 11B, there is no further advancement of the vaginal diagnostic device 2.

Figure 11C:
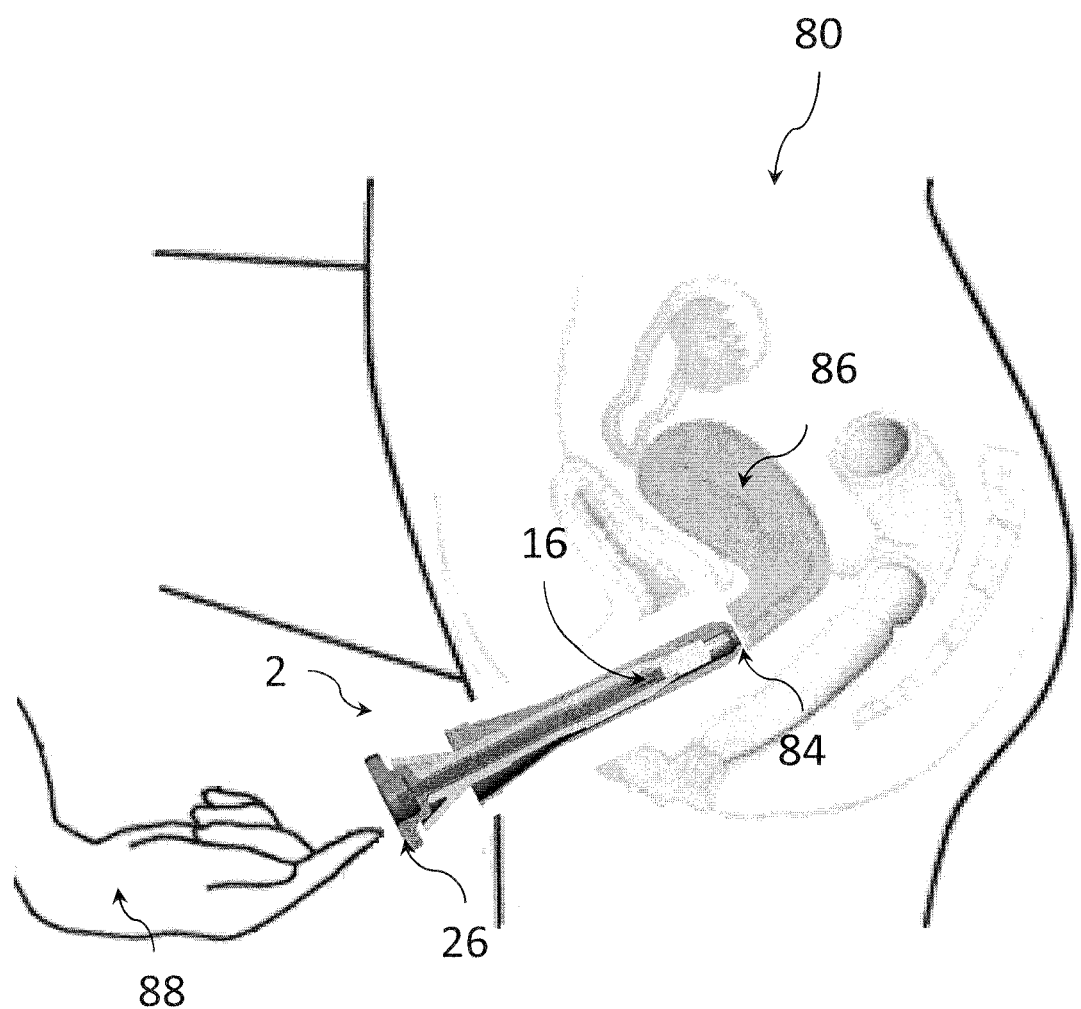
Figure 11D:
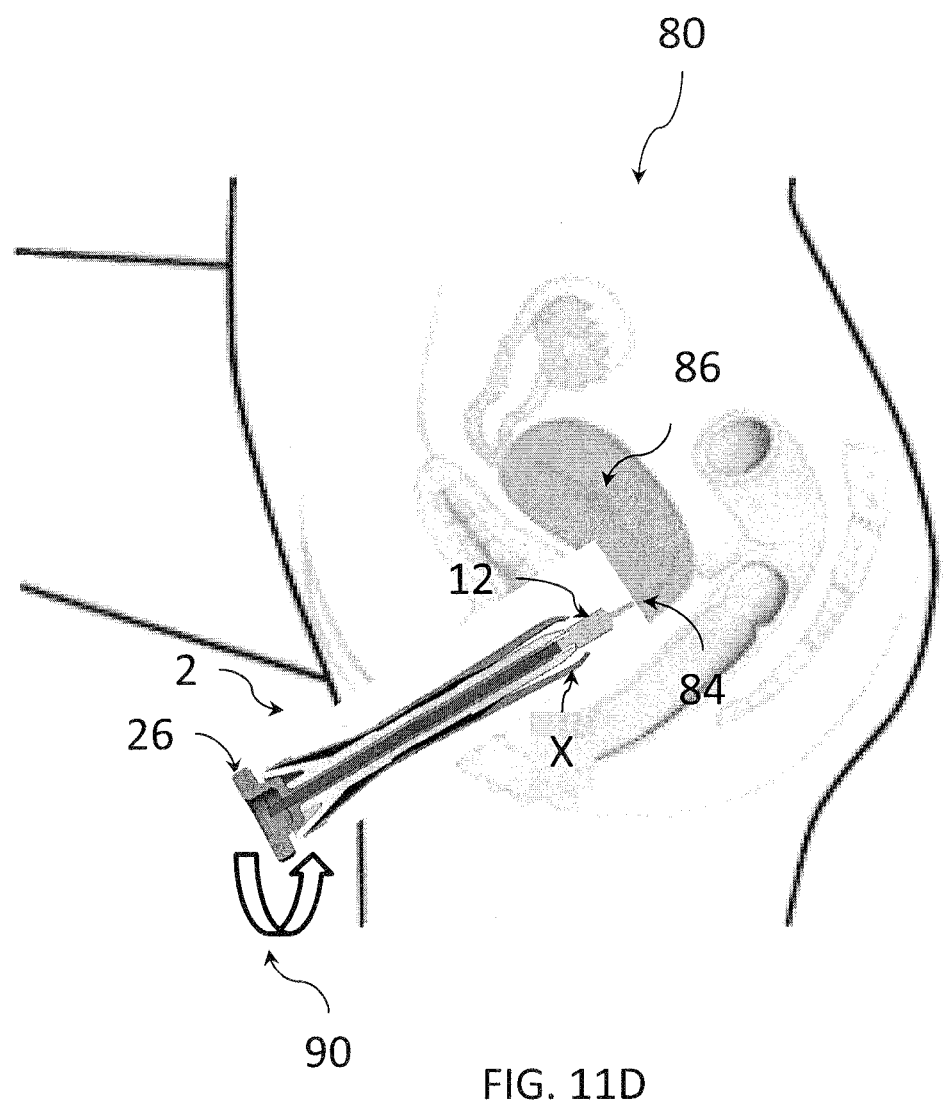
Figure 11E:
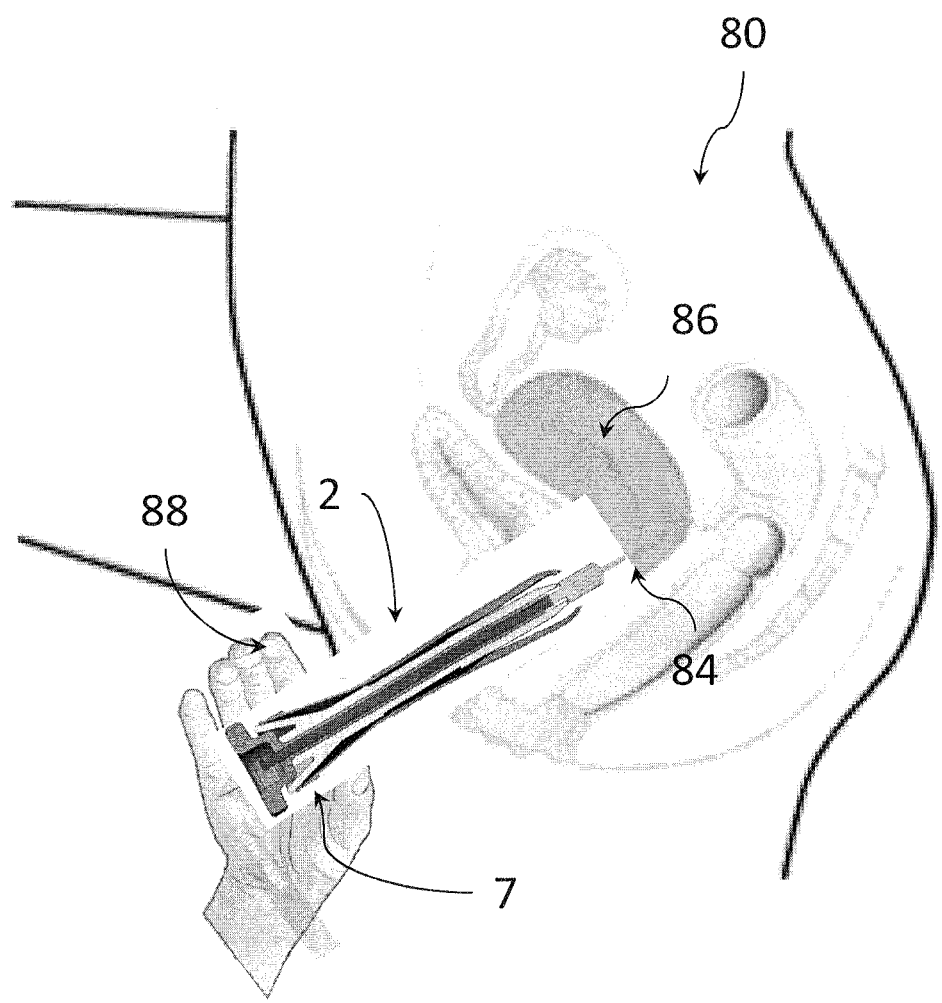

As illustrated in FIG. 11C, when the vaginal diagnostic device 2 is suitably positioned within the female patient 80, the user applies a force to the engagement member 26 using the hand 88 of the user. Because the engagement member 26 is seated within the conical section 28 of the core 16, the force is transmitted to the core 16, causing the core 16 to advance axially within the outer sleeve 4 until the conical section 28 of the core 16 is received in the conical section 6 of the outer sleeve 4. Advancement of the core 16 triggers expansion of the expansion section 10, thus causing the medical diagnostic device 2 to transition from the closed insertion position to the open deployed position. As illustrated in FIG. 11D, when the medical diagnostic device 2 is in the open deployed position, the diagnostic assembly extends. For purposes of this example, the diagnostic assembly can include a sample collecting assembly 19, an imaging device 56, or a combination of the sample collecting assembly 19 and the imaging device 56. In the open deployed position, the user of the diagnostic device 2 manipulates (e.g., rotates) the engagement member 26, which due to the connection between the engagement member 26 and the diagnostic assembly, correspondingly causes the entire diagnostic assembly to rotate. In this specifically illustrated embodiment, the diagnostic assembly is a sample collecting assembly 19 that includes a sample collector 12. In this embodiment, in the deployed position, the sample collector 12 extends and rotation of the engagement member 36 causes the sample collector 12 to rotate and engage the cervix in order to gather a sample. Similarly, when the diagnostic assembly includes an imaging device 56, the imaging device 56 extends and is also permitted to rotate in order to gather image data.

Figure 11F:
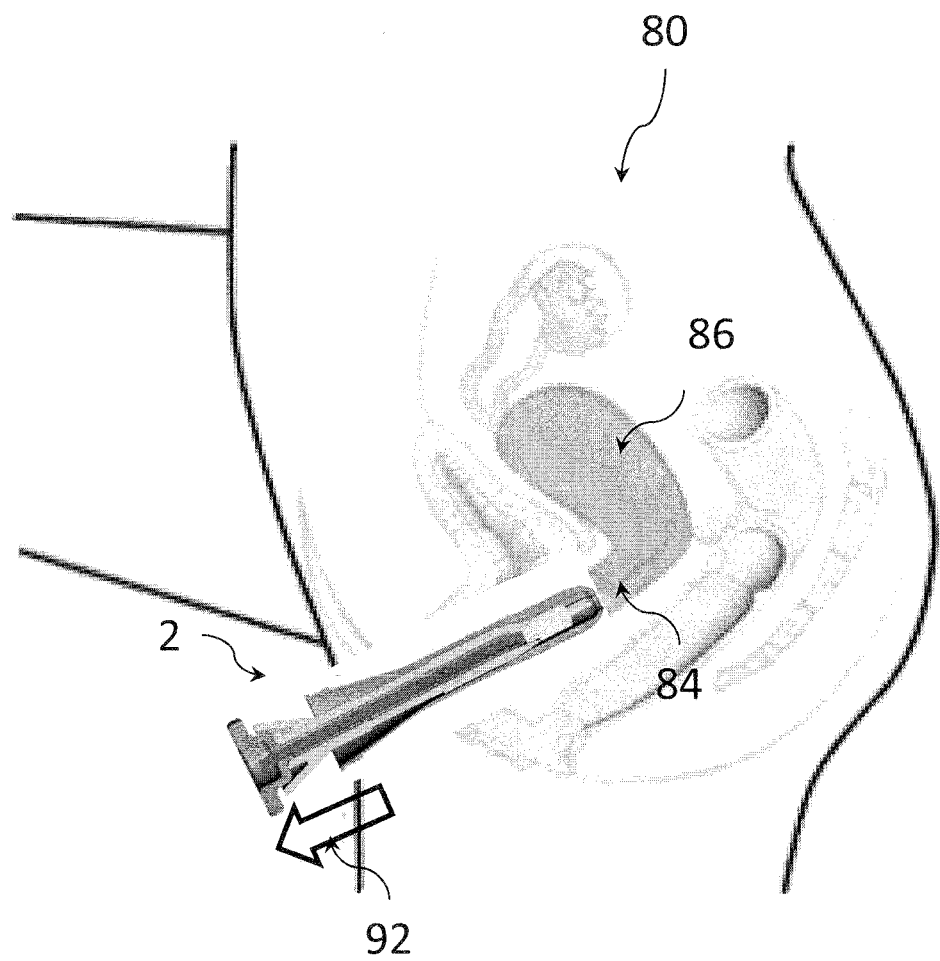
Figure 11G:
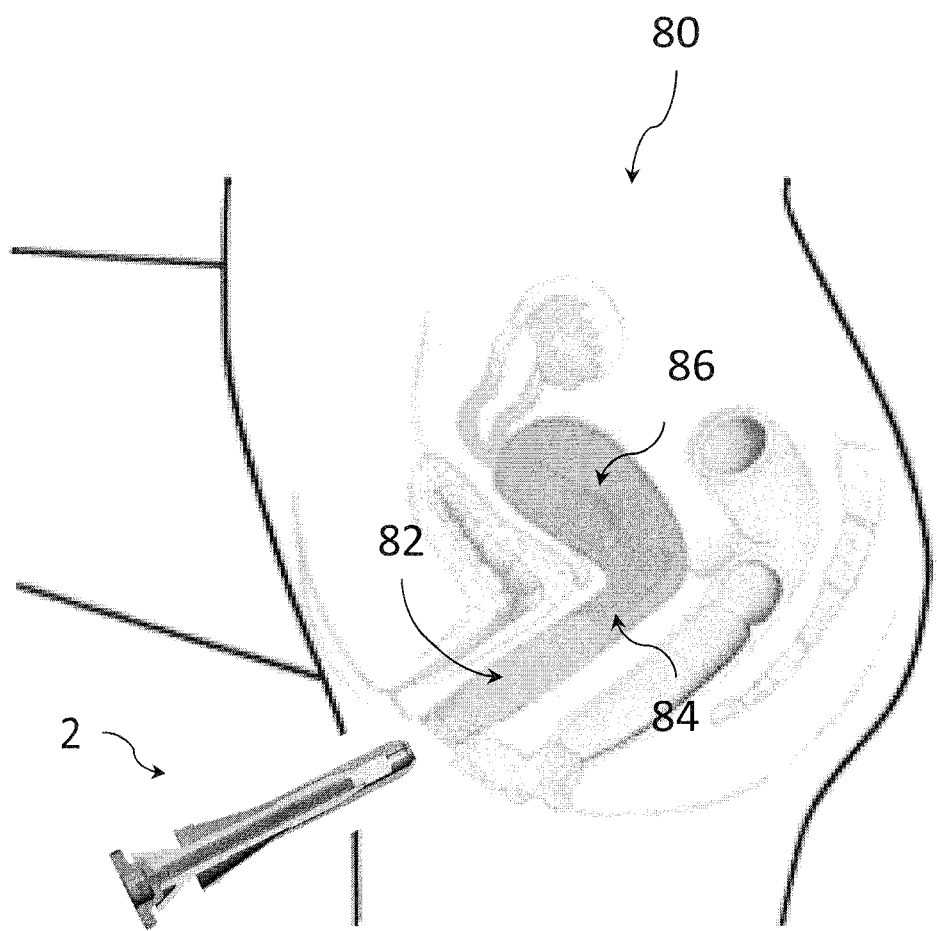
Figure 11H:
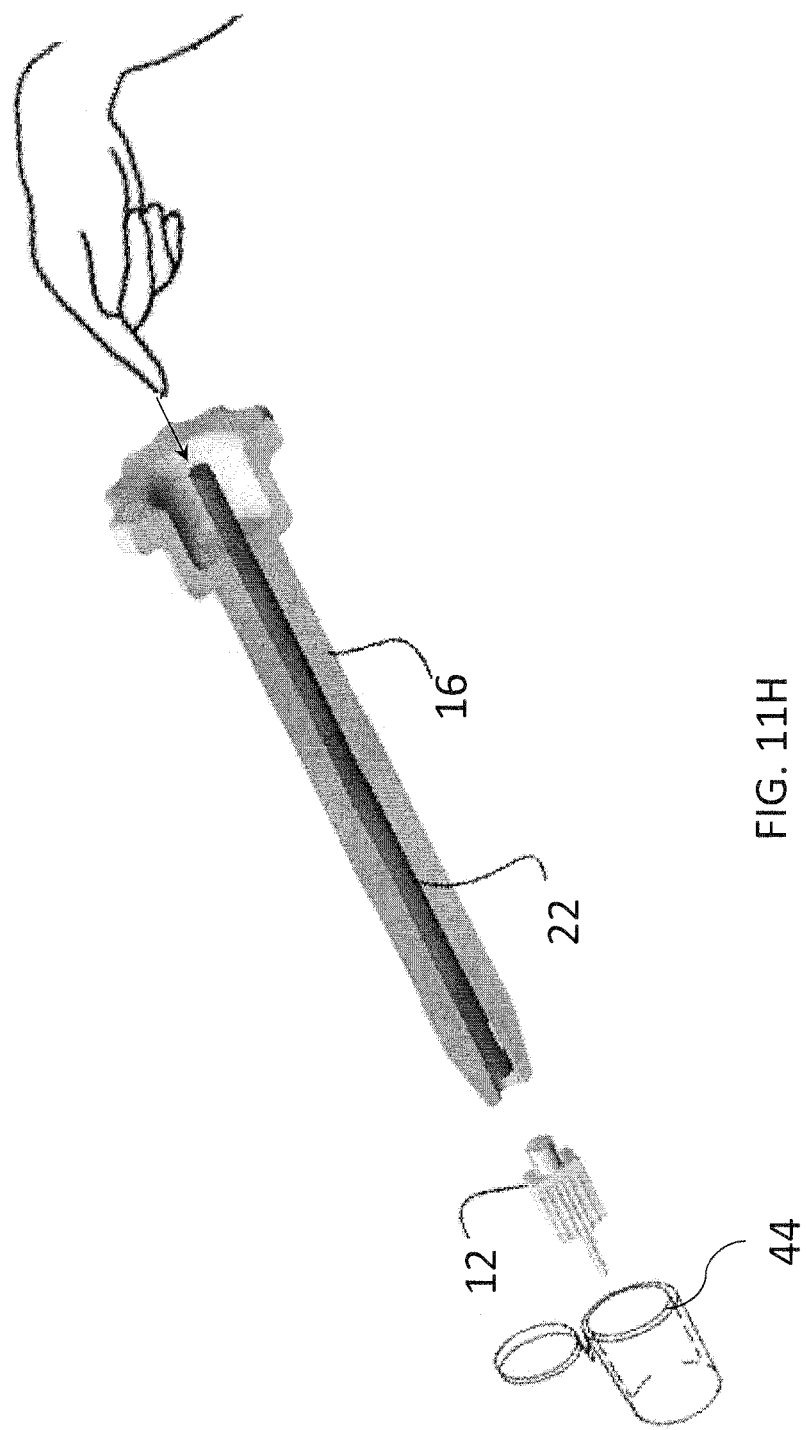

Following collection of the sample (and/or image data), the user compresses the conical section 6 of the medical diagnostic device 2 with the user's hand 88. For example, the female 80 applies a force to the spaced locator pads 20, causing inward depression of the conical section 6 of the outer sleeve 4. This compression of the proximal conical section 7 engages and retracts the core 16 via engagement with the proximal conical portion 28 from the open deployed position to the closed insertion position. During this axial movement, the stop surface 38 of the outer sleeve 4 positively engages the stop groove 40 of the core 16 to prevent the core 16 from further movement and also from ejecting entirely from the outer sleeve 4. Following retraction of the core 16, the user 80 moves the medical diagnostic device 2 downward, in the direction of arrow 92, away from the cervix 84 as illustrated in FIG. 11F. As illustrated in FIG. 11G, the medical diagnostic device 2 is removed from the vagina 82. As illustrated in FIG. 11H, when the diagnostic assembly is a sample collecting assembly, following removal of the medical diagnostic device 2, the patient 80 applies a force to the proximal end of the ejector pin 22. This force causes the ejector pin 22 to release the sample collector 12 from the ejector pin 22 by advancing the sample collector 12 beyond the distal end of the keyed rotatable hollow shaft 24. In an example, the sample collector 12 can be ejected into a sample container 44. This sample container 44 can be sent to a medical professional for analysis. If the diagnostic assembly includes an imaging device 56, the image data gathered by the imaging device 56 can be sent to a medical professional for analysis.

While this method is illustrated herein as employing the vaginal diagnostic device 2A including a sample collector 12, it is to be understood that the method can employ any of the previously described embodiments of the medical diagnostic device 2A, 2B, 2C previously described herein. Further, while the method is described as collecting a vaginal sample, it is to be understood that the herein described medical diagnostic device can collect a sample, image data, or a combination of a sample and image data.

Figure 12:
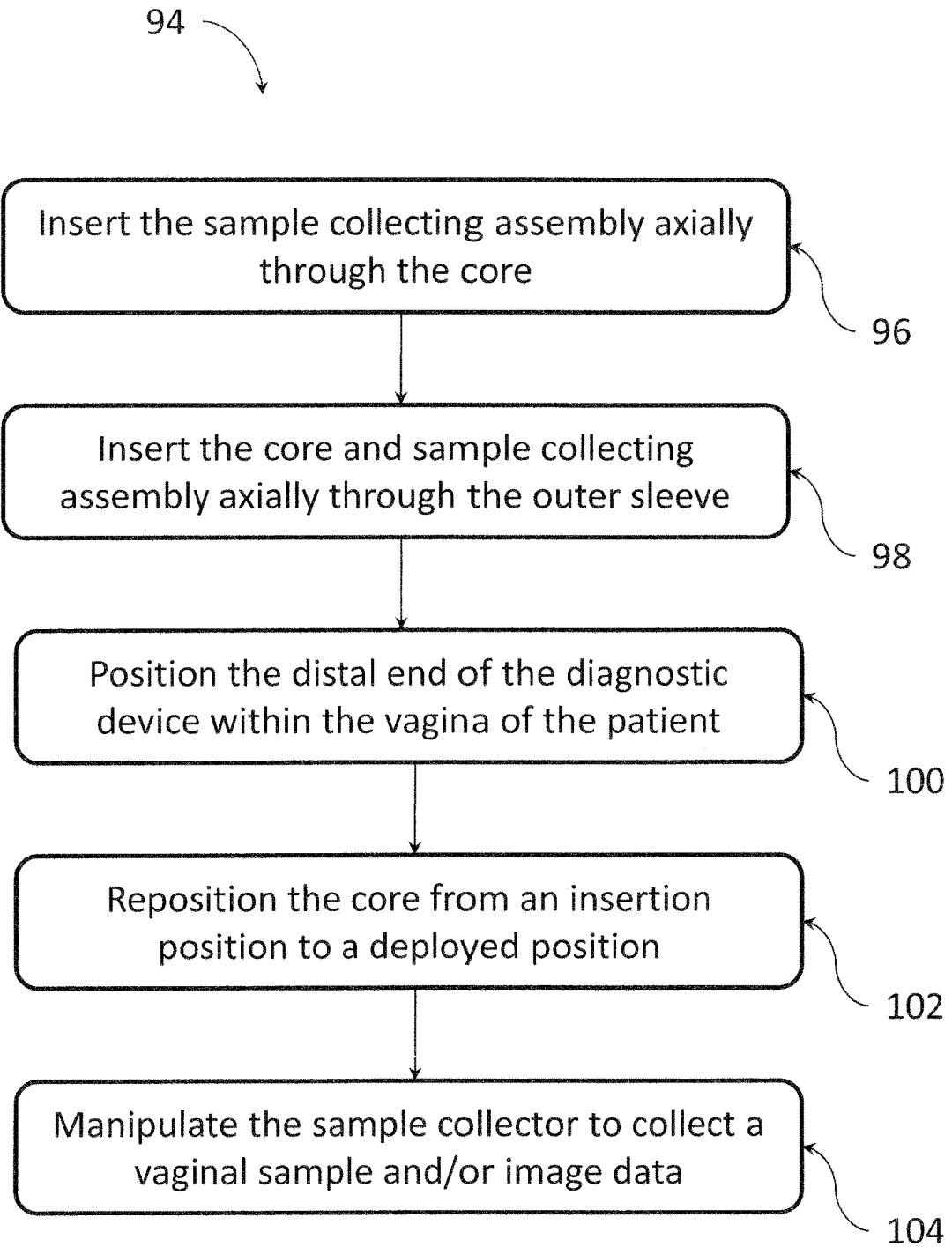
FIG. 12 is a flowchart partially depicting a method of utilizing a medical diagnostic device in accordance with an embodiment.

As illustrated in FIG. 12, a method 94 of utilizing a medical diagnostic device, such as the diagnostic device 2A, 2B, 2C described above, includes, at block 96, inserting a diagnostic assembly axially through a core. In an example, the diagnostic assembly includes a sample collector coupled to an ejector pin that is inserted axially through a rotatable shaft. In another example, the diagnostic assembly is an imaging device. In yet another example, the diagnostic assembly is both a sample collector and an imaging device.

At block 98, the core and diagnostic assembly are inserted axially through the outer sleeve of the medical diagnostic device. At block 100, the distal end of the diagnostic device is positioned within the vagina or other body cavity of the patient. The medical diagnostic device is then advanced through the vagina to the cervix. At block 102, the core is repositioned from an insertion position to a deployed position. At block 104, the diagnostic assembly is manipulated to collect a patient sample and/or image data.

Figure 13A:
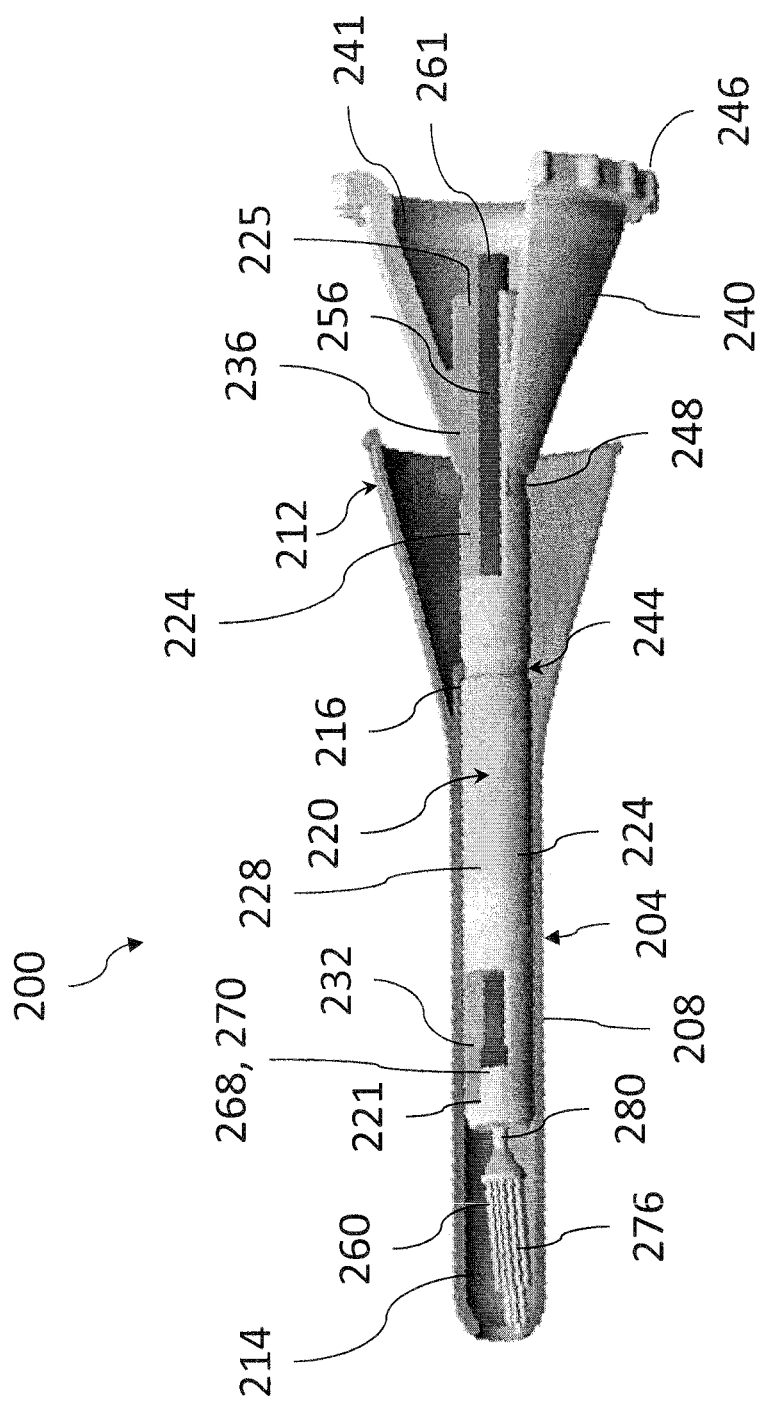
FIG. 13A is a side elevational view of a medical diagnostic device, taken in section, made in accordance with another embodiment and as depicted in an initial non-deployed position.
Figure 13B:
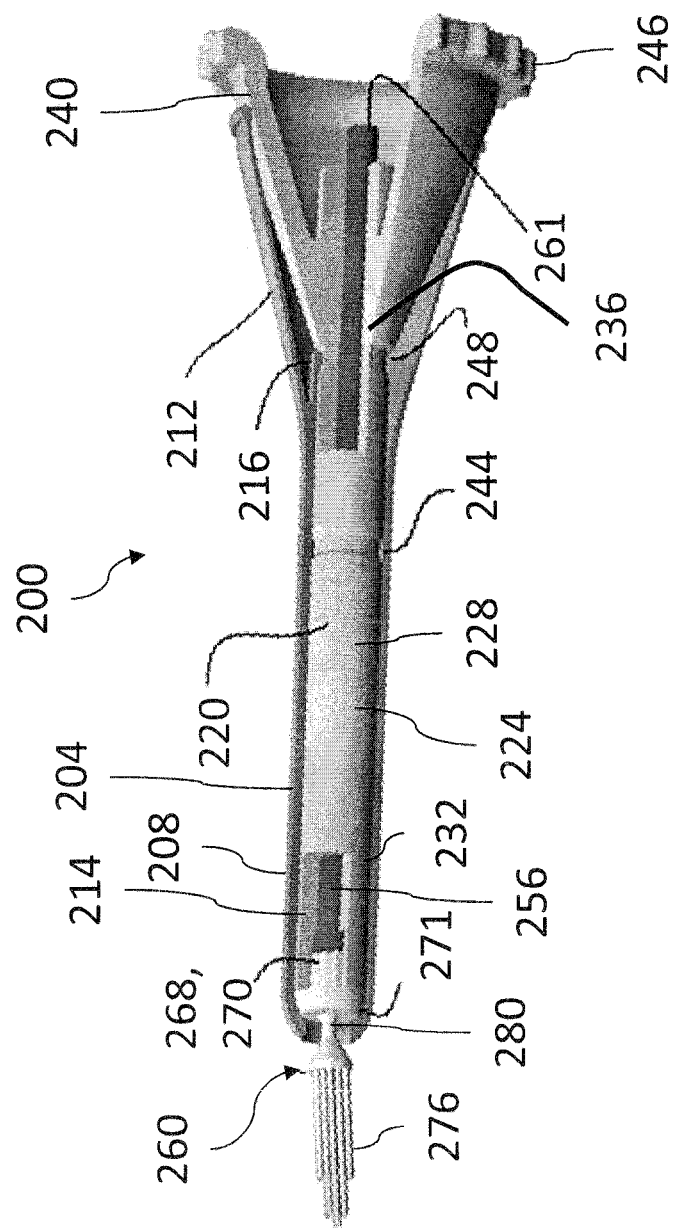
FIG. 13B is the side elevational view of the medical diagnostic device of FIG. 13A, also taken in section, and in which a contained sampling assembly is shown in a deployed position.

With reference to FIGS. 13A and 13B, there is depicted a medical diagnostic device 200 which is made in accordance with another embodiment. The diagnostic device 200 includes an outer sleeve 204 that is defined by a distal portion 208, a proximal portion 212 as well as a hollow interior 214. The majority of the outer sleeve 204, including the distal portion 208, is defined by a substantially tubular configuration having a substantially constant diameter that transitions to the proximal portion 212, the latter being defined by a tapering or substantially conical shape. According to this embodiment, at least one stop surface 216 is provided along an inner surface of the outer sleeve 204 at the transition between the tubular and conical sections 208, 212 of the outer sleeve 204. More specifically, the stop surface 216 can be an axial projection.

A core 220 is positioned within the hollow interior 214 of the outer sleeve 204. The core 220 according to this embodiment is defined by an elongate tubular member 224 that includes an exterior surface 228, as well as respective distal and proximal portions 232, 236. The core 220 further includes a hollow tapering or conical portion 240 extending from the proximal portion 236 of the elongate tubular member 224 and in which the proximal end of the hollow proximal conical portion 240 includes an engagement member 246, which according to this embodiment is in the form of a knob. A pair of stop grooves 244, 248 are provided in the exterior surface 228 of the core 220 in spaced relation. In an initial position, the stop surface 216 is engaged with a distal stop groove 244, also as shown in FIG. 13A, which prevents the core 220 from being retracted outwardly beyond a predetermined axial position.

Figure 14A:
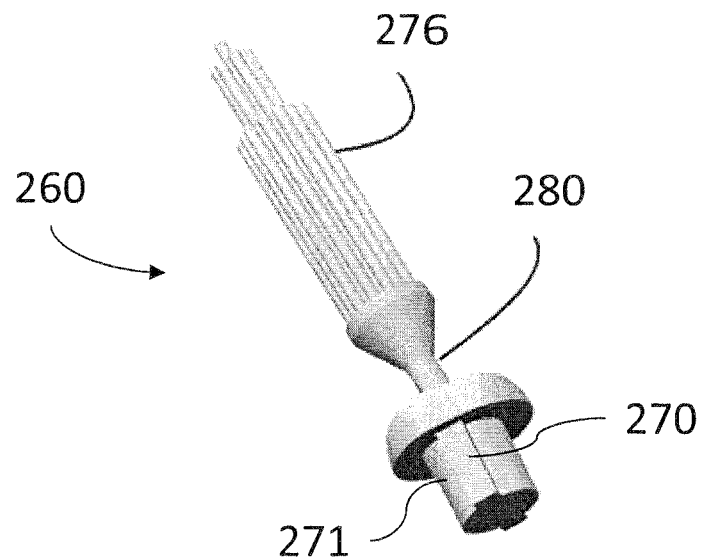
FIG. 14A is the side perspective view of the sampling assembly of the medical diagnostic device of FIGS. 13A and 13B.

Still referring to FIG. 13A and extending from an axial opening 221 formed in the distal end of the core 220 is a sampling device 260 that is formed as part of a diagnostic assembly, the remainder of which is initially provided and retained within the core 220. The diagnostic assembly, according to this embodiment, includes an ejector rod 256 having a proximal end 261 that extends initially from the proximal end 225 of the elongate tubular member 224 and within a recess 241 that is formed in the hollow proximal conical portion 240. The ejector rod 256 is axially movable within the core 220, the distal end of the core 220 further supporting a sample collecting device 260. With reference to FIGS. 13A and 14A, the distal end of the core 220 includes at least one keyway 268 that is configured to engage a corresponding number of keys 270 radially extending from a proximal or coupling portion 271 of the sample collecting device 260. According to this embodiment, the sample collecting device 260 is a brush having a series of circumferentially disposed bristles 276 at its distal end. According to this embodiment, the sampling device 260 is further defined by a shaft 280 disposed between the bristles 276 and the coupling portion 271 that is angled relative to a common primary axis defined by the core 220 and the outer sleeve 204, when assembled, and as shown in FIG. 13A. Alternatively, the shaft could form a curved section relative to the primary axis of the assembly.

In a second or deployed position, shown in FIG. 13B and after the diagnostic device 200 has been implanted into the body cavity (e.g., vagina) of a patient (not shown), the core 220 is advanced axially toward the distal end of the outer sleeve 204, which advances the sample collecting device 260 through a formed distal opening of the outer sleeve 204. Axial movement proceeds until the stop surface 216 engages the second spaced stop groove 248, the latter groove 248 being disposed adjacent the transition of the conical portion 240 of the core 220. In this position, the substantially conical sections 212, 240 of the outer sleeve 204 and core 220 are nested. The angled shaft 280 of the sample collecting device 260 better insures the ability of the sample collecting device 260 and more specifically the disposed bristles 271 to engage the surface of the cervix (not shown) in order to obtain a suitable sample through rotation of the core 220 as accessed using the engagement member 246. As shown in FIG. 14A, the proximal end of the sample collecting device 260 includes a coupling portion having a pair of radially disposed keys 286 that are aligned with corresponding keyways 268 at the end of the ejector rod 256. In this position, the keys 270 and keyways 268 are still engaged within the distal end of the core 220, thereby retaining the sample collecting device 260 in use.

To eject the sample collecting device 260, the proximal end of the ejector rod 256 is axially advanced by the user (not shown), which advances the coupling portion of the sample collecting device 260 from the core 220 and the outer cavity 204. Prior to ejection, the formed recess 241 of the hollow conical portion 240 protects inadvertent contact with the projecting end 261 of the ejector rod 256 when the diagnostic device 200 is still in use and prevents premature ejection of the sample collecting device 260.

Figure 14B:
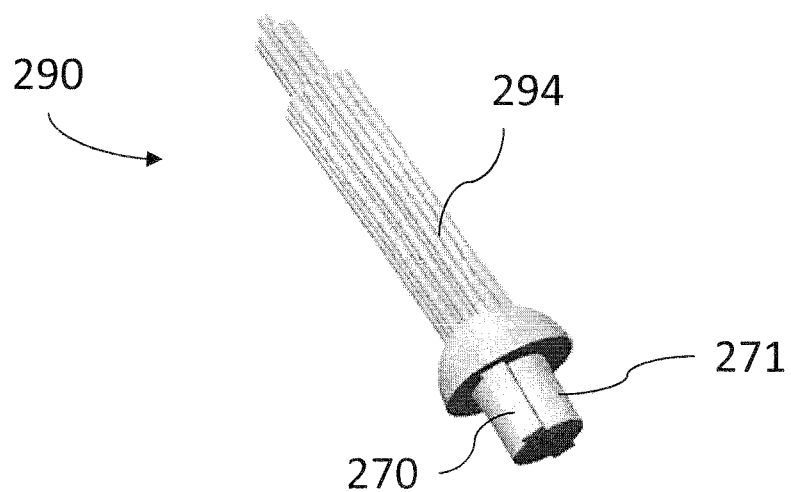
FIG. 14B is a side perspective view of a sampling assembly in accordance with another embodiment.

With reference to FIGS. 14(a) and 14(b), the shoulder above the key is sized according to this specific embodiment so as not to allow passage through the distal end of the outer sleeve 204. The foregoing feature is provided chiefly to insure patient safety.

An alternative sample collecting device 290 is shown in FIG. 14B. According to this version, the sample collecting device 290 is a brush that is defined with angled bristles 294 extending from the distal end of the sample collecting device 290 when in the deployed position. As in the preceding version, this device also includes a coupling portion at a proximal end having a set of keys (or keyways) configured for engaging corresponding keyways formed at the distal end of the core 220.

Reference is herein made to FIGS. 15-18, depicting yet another embodiment of a medical (vaginal) diagnostic device 300. The diagnostic device 300 is defined by an outer sleeve 304 having a distal portion 308 and a proximal portion 312, as well as a hollow interior 314. The majority of the outer sleeve 304, including the distal portion 308 is defined by a substantially tubular configuration having a constant diameter that transitions to the proximal portion 312, the latter being defined by an outwardly tapering or substantially conical shape. At least one stop surface 316, in this instance, at least one axial projection is provided along an inner surface of the outer sleeve 304 at the transition between the tubular and conical sections 308, 312 of the outer sleeve 304.

A core 320 (also herein referred to synonymously as an obturator) is positioned within the hollow interior 314 of the outer sleeve 304. 304. The core 320 according to this embodiment is defined by an elongate tubular member 324 that includes an exterior surface 328, as well as respective distal and proximal portions 332, 336. The core 320 further includes a hollow tapering or conical portion 340 that outwardly and radially extends from the proximal portion 336 of the elongate tubular member 324 and in which a proximal end of the hollow proximal conical portion 340 includes an engagement member 346, which according to this embodiment is a formed knob and in which the hollow proximal conical portion 340 is further defined by a formed recess 341. A pair of stop grooves 344, 348 are provided in the exterior surface 328 of the core 320 in spaced relation. In an initial position, the stop surface 316 is engaged with a distal stop groove 344, as shown in FIG. 15 which prevents the core 320 from being retracted beyond a predetermined axial position, as shown.

Figure 15:
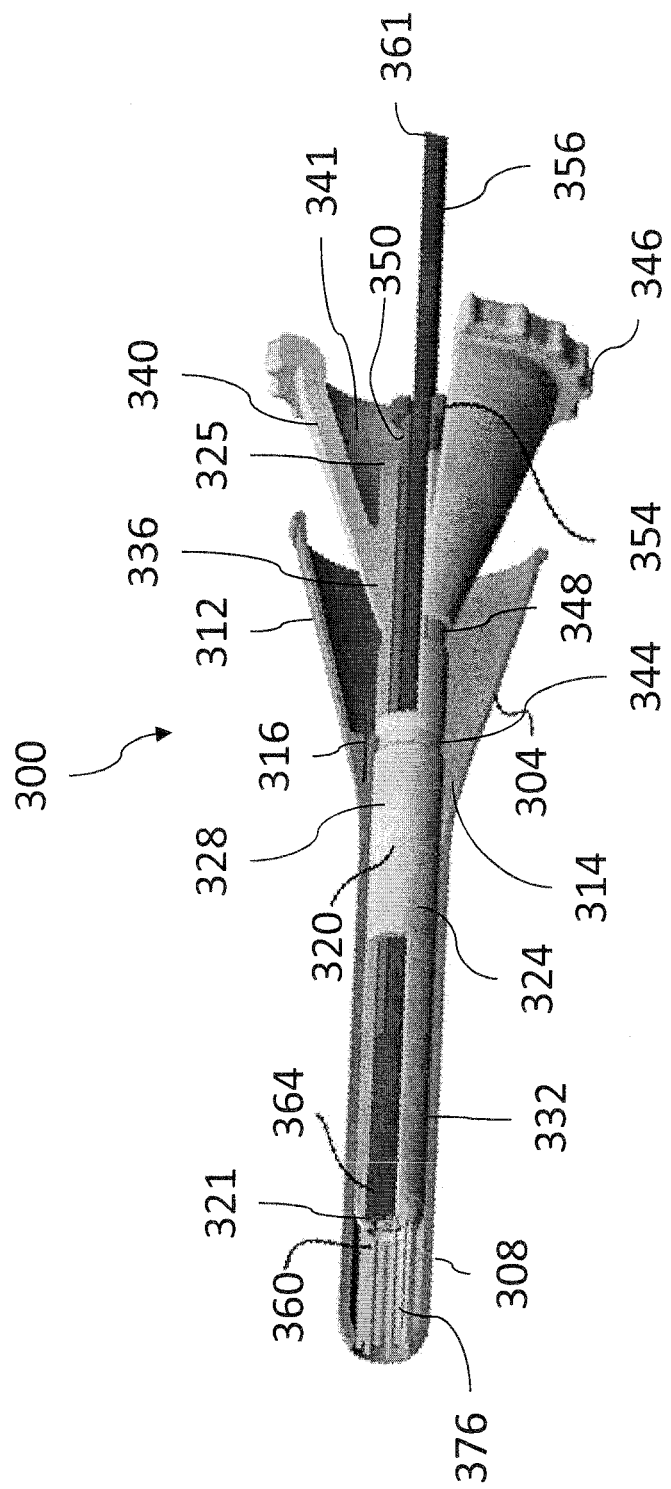
FIG. 15 is a side elevational view, taken in section, of a medical diagnostic device made in accordance with yet another embodiment.

Still referring to FIG. 15 and extending from an axial opening 321 formed in the distal end of the core 320 is a sampling device 360 that is formed as part of a diagnostic assembly, the remainder of which is provided and retained within the interior of the core 320. The diagnostic assembly according to this embodiment includes a rotatable ejector rod 356 having a proximal end 361 that extends initially from the proximal end 325 of the elongate tubular member 324 and the recess 341 of the hollow proximal conical portion 340. An opposing distal end 364 of the ejector rod 356 extends into the distal end of the core 320 and is configured to engage the sample collecting device 360, such as a brush having a series of distally disposed bristles 376. According to this embodiment, the sample collecting device 360 includes a proximal or coupling end that includes a pair of keys 370 or other connecting means that engage with corresponding slots or keyways 368 that are formed in the distal end of the core 320.

Figure 18:
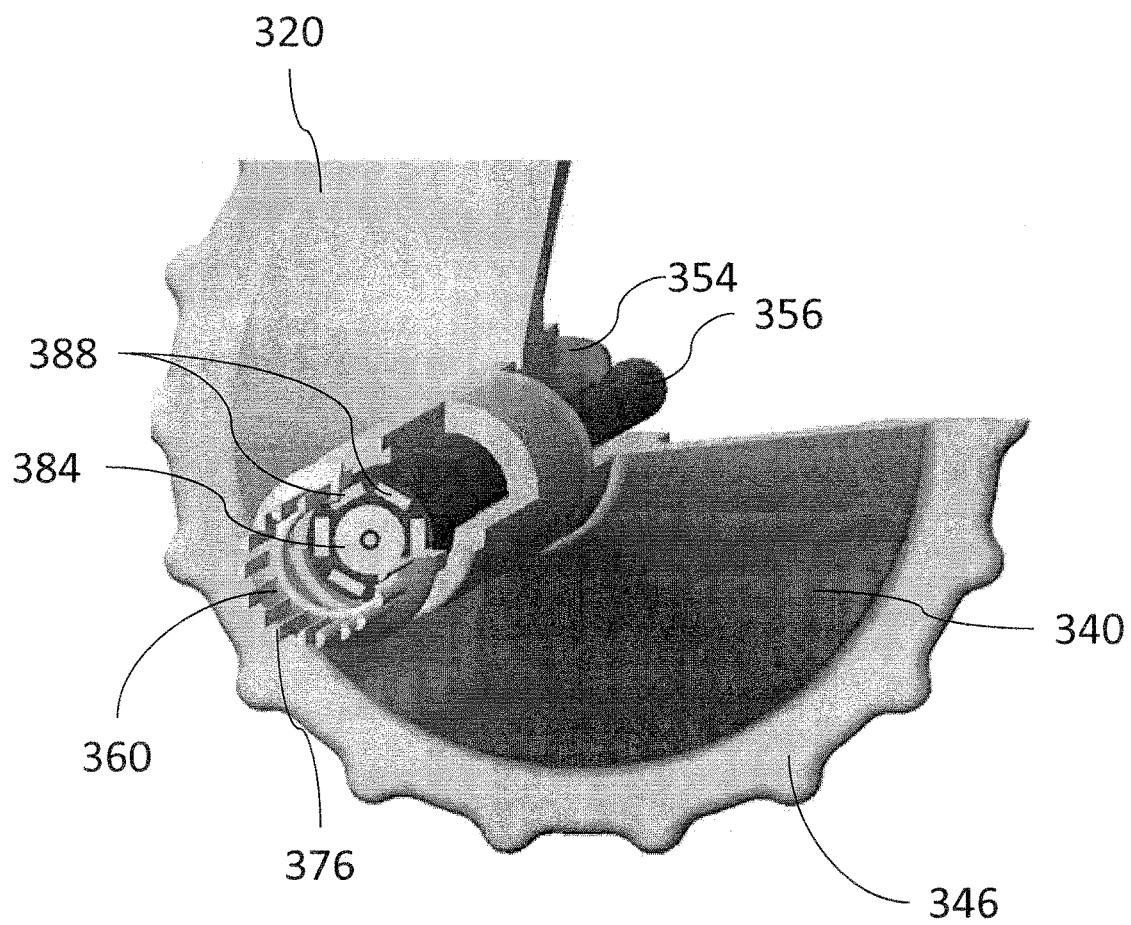
FIG. 18 is a partial perspective distal end view of the medical diagnostic device of FIGS. 16-17.

According to this embodiment, the distal end of the ejector rod 356 is further configured to support an imaging assembly 384, as shown most specifically in FIG. 18, including an electronic imager disposed in relation to the bristles 376 of the sample collecting device 360 as well as a plurality of LEDs 388 that are circumferentially disposed as a ring about the imager to provide sufficient illumination of the target of interest. Preferably, the bristles 376 of the sampling device 360 are made from a non-reflective material in order to more efficiently illuminate the target of interest (e.g., cervix) for viewing wherein the imaging assembly includes a wired or wireless connection in order to transmit images. The imaging assembly 384 and the illumination assembly 388 can be powered by means of a battery (not shown) using, for example, a USB connection. Alternatively, self-contained power sources can be provided.

According to this embodiment, the imaging assembly 384, including the shaft, is prevented from inadvertently retracting from the proximal end of the device 300 by means of a retainer 350 that is disposed between the elongate tubular member 325 of the outer sleeve 304 and the outer surface of the shaft 356, the retainer 350 having a compressive clamp 354 at a proximal end thereof.

Figure 16:
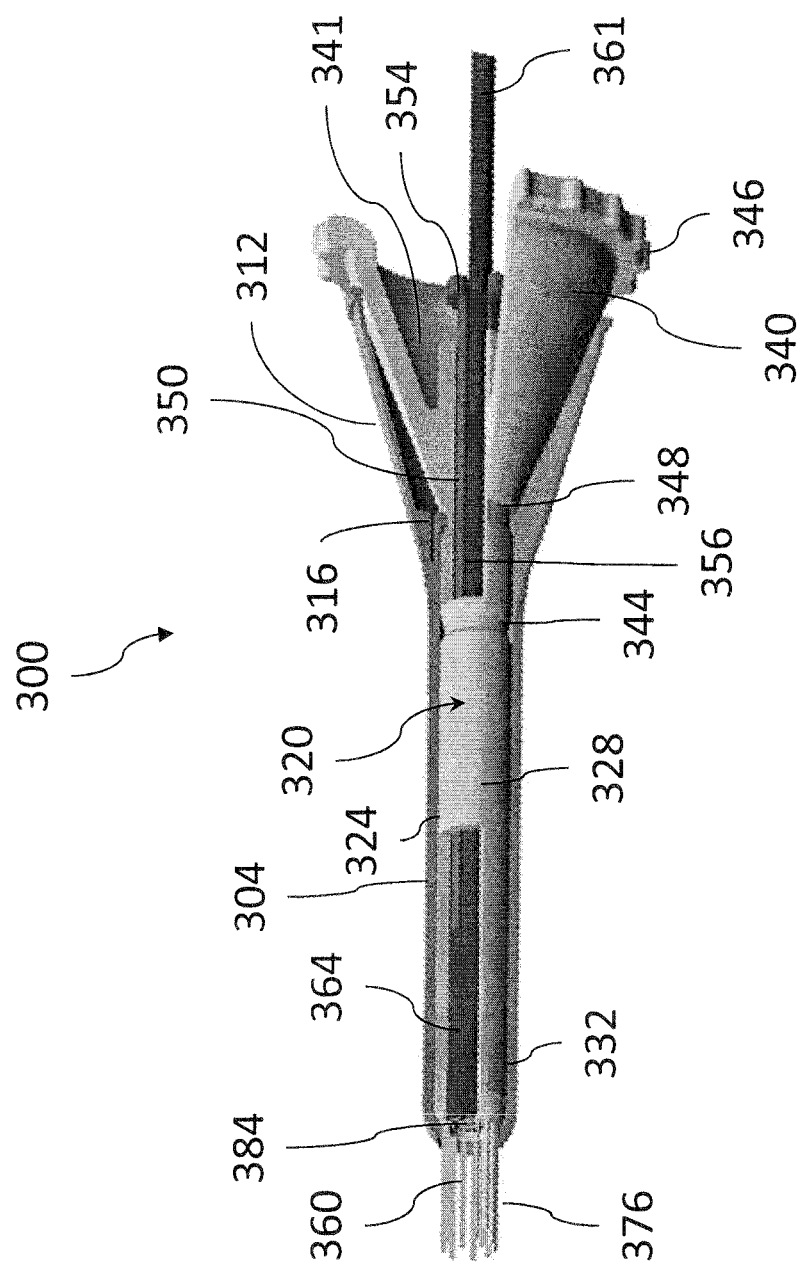
FIG. 16 is the side elevational view of the medical device of FIG. 15, also in section, depicting a sampling assembly of the diagnostic device in a deployed position.

In a deployed position, shown in FIG. 16 and after the diagnostic device 300 has been implanted into the body cavity (e.g., the vagina) of a patient (not shown), the core 320 is advanced axially toward the distal end of the outer sleeve 304, which advances a portion of the sample collecting device 360, including the bristles 376, through a formed distal opening of the outer sleeve 304 and further positions the imaging assembly 384 at the distal opening of the outer sleeve 304. According to this embodiment, axial movement proceeds until the stop surface 316 engages the second spaced stop groove 348, the latter groove 348 being disposed adjacent the transition of the conical proximal portion 340 of the core 320. In this position, the substantially conical sections 312, 340 of the outer sleeve 304 and the core 320 are nested. The core 320 is then rotated using the engagement member 346 to enable the sample collecting device 360 to corresponding rotate about the axis of the core 320 to collect a suitable sample from the wall of the body cavity and in which the sampling operation can be viewed using the imager assembly 384, the latter assembly being fixed and prevented from rotation by the retainer 350.

Figure 17:
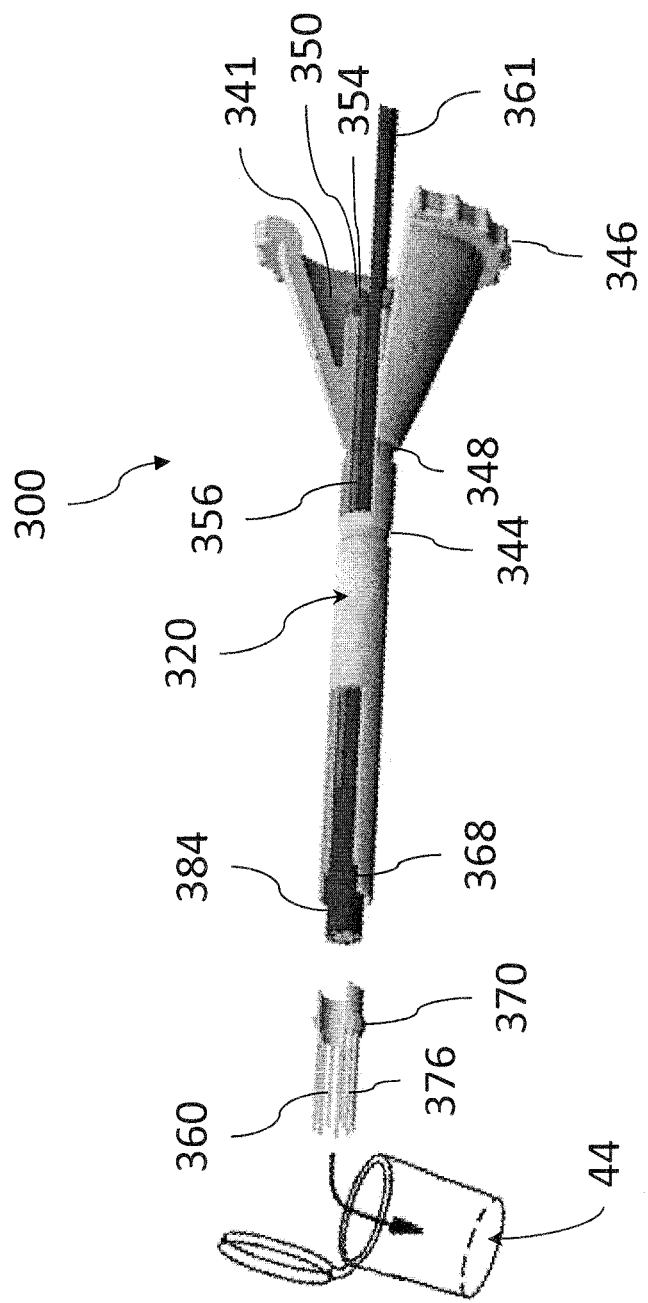
FIG. 17 is a side elevational view, shown in section, of the medical diagnostic device of FIGS. 15 and 16, depicting the ejection of a sample collecting device.

With reference to FIG. 17, the ejection of the sample collecting device 360 from the diagnostic device 300 is depicted. In this figure, the outer sleeve is not shown for the sake of clarity. To eject the sample collecting device 360 the proximal end of the ejector rod 356 is axially advanced toward the distal end of the diagnostic device 300, which advances the ejector shaft against a shoulder of the sample collecting device 360 and further advances the keys 370 of the coupling portion from the keyways 368 at the distal end of the core 320. As a result, the sample collecting device 360 is released from the assembly 300 and deposited in a suitable sample container 44. The recess 341 of the hollow conical portion 340 protects inadvertent contact with the ejector rod 356 when the device 300 is still in use and prevents premature ejection of the sample collecting device 360.

Figure 19A:
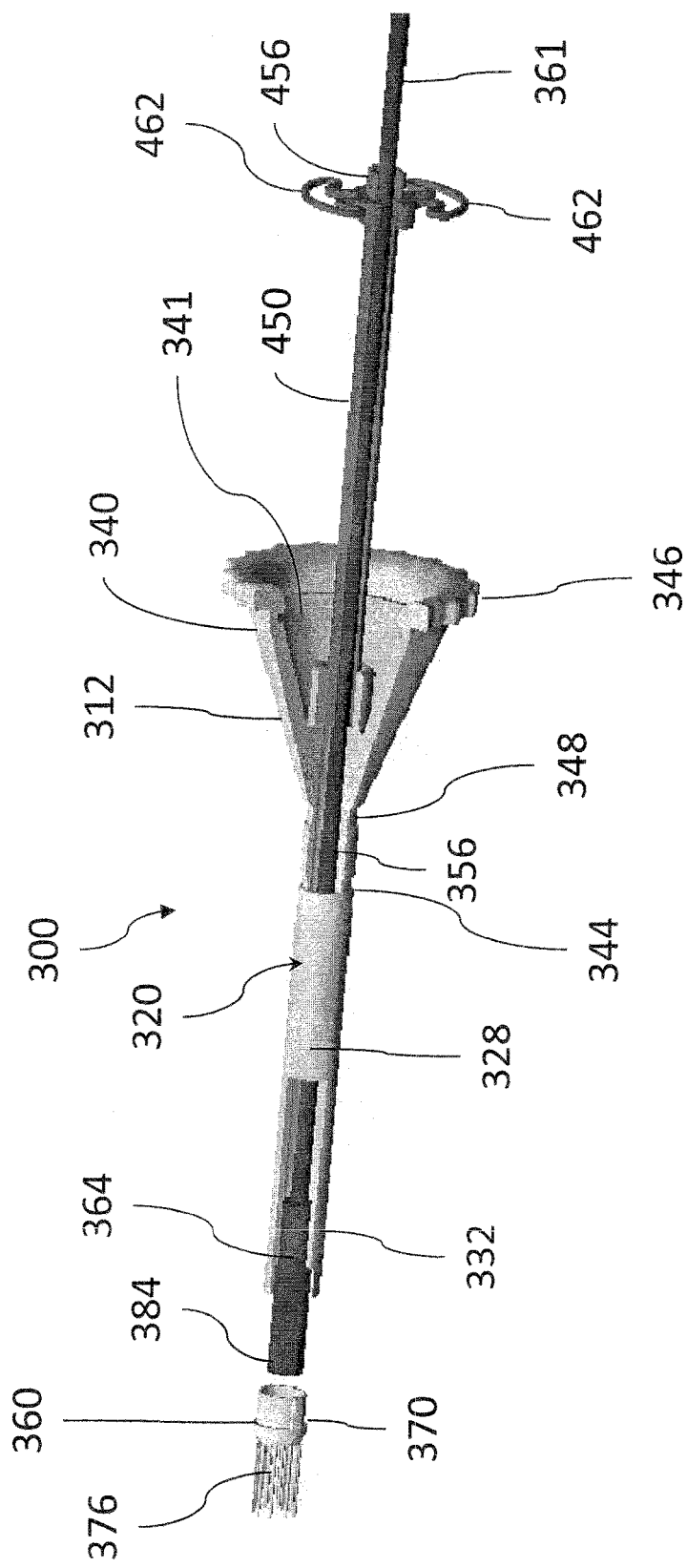
FIG. 19A is an exploded partial assembly view of a medical diagnostic device including a retainer made in accordance with another embodiment.
Figure 19B:
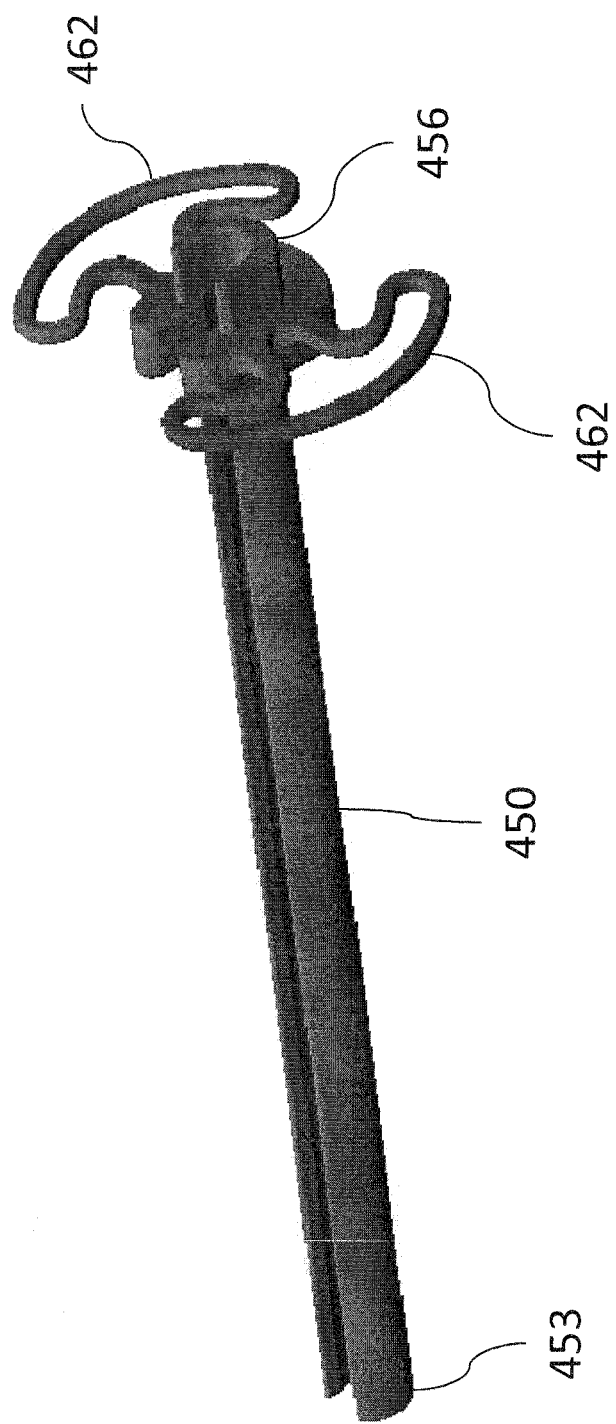
FIG. 19B is a perspective view of the retainer of FIG. 19A.
Figure 19C:
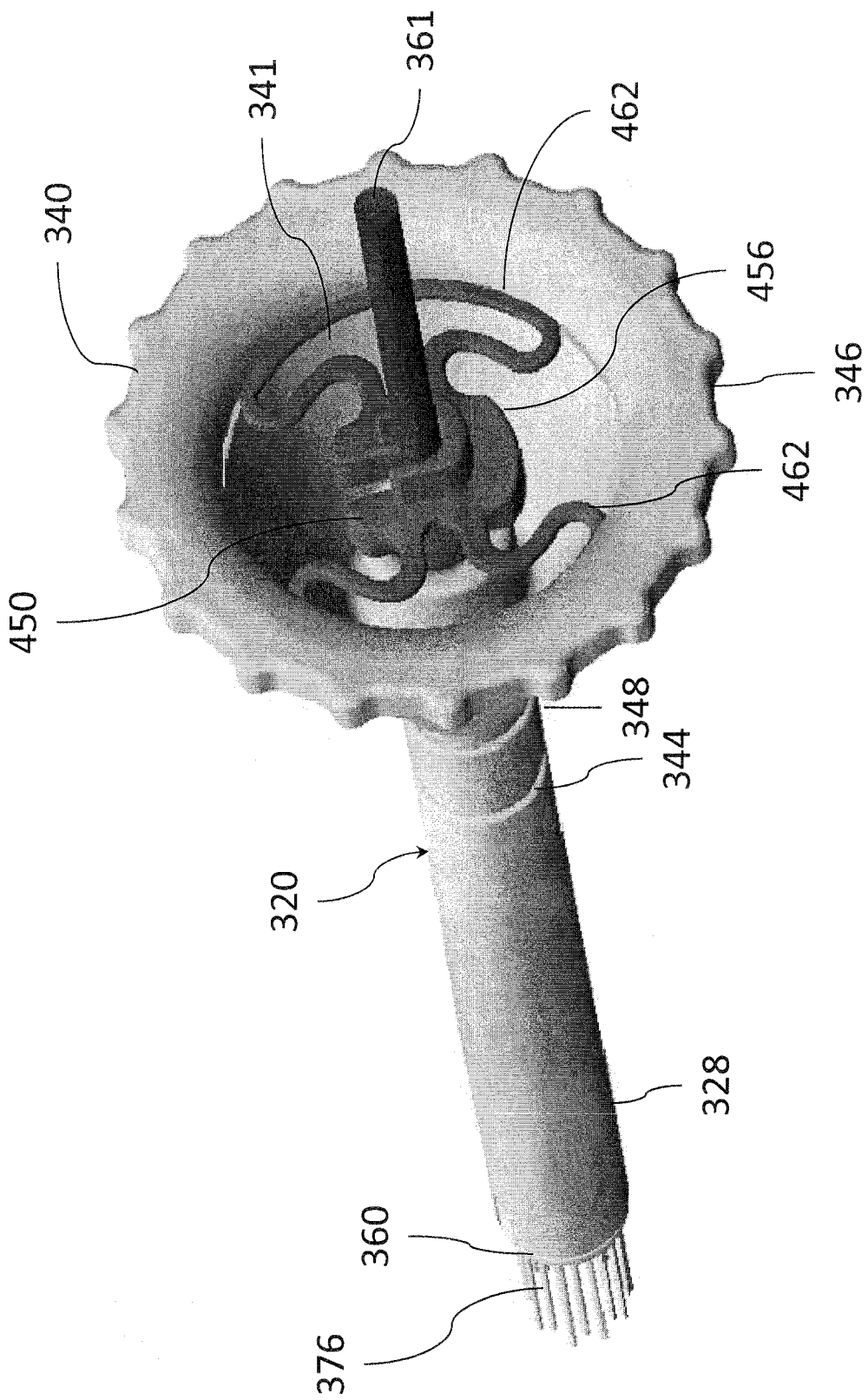
FIG. 19C is a perspective partial assembled view of the medical diagnostic device, including the retainer of FIGS. 19A and 19B.

With reference to FIGS. 19A-19C, another retainer version is herein depicted for use with the assembly 300. Similar parts are herein labeled with the same reference numerals for the sake of clarity. More specifically, the depicted retainer 450 is defined by a hollow and substantially tubular structure having respective distal and proximal ends 453 and 456 as well as a pair of engaging portions 462 adjacent the proximal end 456 that extend radially outward from the tubular structure. Each of the engaging members 462 according to this embodiment are defined by flexible curved sections that are sized to engage an undercut formed within the recess 341 of the conical portion 340 of the core 320 and compressively engage against the inner surface of the conical section 340 when fitted with the cabling of the imaging assembly being supported by the hollow tubular structure of the retainer 450.

In operation, the sampling device 360 can be keyed for rotation, as described, when acted upon by the engagement member 346 in the same manner previously described. During rotation, the imaging assembly 384 being secured by the retainer 450 is prevented from rotating. In the meantime, the flexible engaging members 462 prevent the imaging assembly 384 from prematurely retracting from assembly 300 and more specifically proximally from the core 320. It will be readily apparent that the number of flexible engaging members can be varied provided the members are capable of providing sufficient radial/torsional force to prevent free axial movement of the imaging assembly 484. Upon completion of a sampling operation and as previously discussed, ejection can occur based on inward flexion of the retainer 450 in combination with axial movement of the imaging assembly 384.

PARTS LIST FOR FIGS. 1-18

1 device proximal end
2 medical diagnostic device 2A medical diagnostic device
2B medical diagnostic device
2C medical diagnostic device
3 distal end, diagnostic device
4 outer sleeve
6 substantially conical section (outer sleeve)
8 distal section (outer sleeve)
9 hollow interior (outer sleeve)
10 expansion section
11 fingers, expansion section
12 sample collector
13 axial cuts
14 elastically deformable sheath
16 core
17 axial cavity, core
18 proximal end
19 sample collecting assembly
20 locator pads
22 ejector pin
24 hollow rotatable shaft
26 engagement member
27 distal section, core
28 proximal section, core
30 recessed center portion
31 bristles
32 coupling portion
34 keyways
36 keys
38 stop surface
40 stop groove
42 opening
44 sample container
52 connection
56 imaging device
58 computing device
80 female patient
82 vagina
83 arrow
84 cervix
86 uterus
88 hand
90 rotation
92 arrow
94 method
96-104 method blocks
200 medical diagnostic device
204 outer sleeve
208 distal portion, outer sleeve
212 proximal portion, outer sleeve
214 hollow interior
216 stop surface
220 core
221 axial opening, core
224 elongate tubular member
225 proximal end, elongate tubular member
228 exterior surface, core
232 distal portion
236 proximal portion, elongate tubular member
240 tapering or conical section
241 recess, proximal conical section
244 stop groove, distal
246 engagement member
248 stop groove
256 ejector rod or shaft
260 sample collecting device
261 proximal end, ejector rod or shaft
268 keyways
270 keys
271 coupling portion
276 bristles
280 shaft, angled
290 sample collecting device
294 bristles, angled
300 medical diagnostic device
304 outer sleeve
308 distal portion, outer sleeve
312 proximal portion, outer sleeve
314 hollow interior, outer sleeve
316 stop surface, outer sleeve
320 core
321 axial opening, core
324 elongate tubular member, core
325 proximal end, elongate tubular member
328 exterior surface, core
332 distal portion, elongate tubular member
336 proximal portion, elongate tubular member
340 hollow tapering or conical portion
341 recess, hollow conical portion
344 stop groove, distal
346 engagement member
348 stop groove
350 retainer
354 compressive clamp
356 ejector rod or shaft
360 sample collecting device
361 proximal end, ejector rod or shaft
368 keyways
370 keys
376 bristles
380 shaft
384 imaging assembly
388 LEDs
450 retainer
453 distal end, retainer
456 proximal end, retainer
462 flexible engaging members, retainer While particular variations and illustrative figures having been used in the foregoing description, those of ordinary skill in the art will recognize that the variations and figures are not intended to be limiting. In addition, where methods and steps described above indicate certain events occurring in certain order, those of ordinary skill in the art will recognize that the ordering of certain steps may be modified and that such modifications are in accordance with those as would be apparent to a person of suitable skill in the field. Additionally, certain of the steps may be performed concurrently in a parallel process when possible, as well as performed sequentially as described above. Therefore, to the extent there are variations, which are within the spirit of the disclosure or equivalent to recited features in the claims, it is the intent that this patent will cover those variations as well.

What is claimed is:

1. A medical device comprising:
an outer sleeve having a hollow interior and open distal and proximal ends, the outer sleeve including a proximal section having a substantially conical shape;
a core configured to be inserted axially within the hollow interior of the outer sleeve, the core including an axial inner cavity, the core further including a proximal section having a conical shape substantially conforming to that of the proximal section of the outer sleeve; and a sample collecting assembly comprising:
- a hollow rotatable shaft extending through the axial inner cavity of the core, the shaft having an engagement member positioned at a proximal end of the shaft;
- an ejector pin extending through the hollow rotatable shaft; and
- a sample collector distally coupled to the ejector pin, wherein axial movement of the conical proximal section of the core into the substantially conical proximal portion of the outer sleeve causes deployment of the sample collecting assembly and in which a compressive force applied to the substantially conical proximal section of the outer sleeve causes the proximal section of the core and the sample collecting assembly to be axially retracted.

2. The medical device of claim 1, wherein the ejector pin includes at least one retention feature.

3. The medical device of claim 1, wherein the outer sleeve further comprises a distal expansion section that is configured to transition between a closed position and an open deployed position when the conical proximal section of the core is axially moved into the substantially conical proximal section of the outer sleeve.

4. The medical device of claim 3, wherein the distal expansion section comprises a plurality of fingers which are movable between the closed position and the open deployed position based on the axial movement of the core.

5. The medical device of claim 4, further comprising a flexible sheath extending over the plurality of fingers.

6. The medical device of claim 1, wherein the substantially proximal conical section of the outer sleeve comprises at least two locator pads spaced apart from each other circumferentially to facilitate compression.

7. The medical device of claim 1, wherein the ejector pin is selectively engageable to axially advance the ejector pin and eject the sample collector from the sample collecting assembly.

8. The medical device of claim 7, wherein the engagement member is a rotatable knob that comprises a recessed center portion sized to retain the ejector pin in a safety position to prevent unintentional ejection of the sample collector.

9. The medical device of claim 1, wherein the sample collector comprises a coupling portion configured to releasably couple the sample collector to a distal end of the ejector pin, the coupling portion comprising one of a keyway and a key and the distal end of the ejector pin comprising the other of the keyway and the key to facilitate rotation of the sample collector.

10. The medical device of claim 1, wherein the sample collector comprises a brush.

11. The medical device of claim 1, further comprising an imaging device extending through the axial cavity of the core.

12. The medical device of claim 1, further comprising at least one stop surface positioned on an inner surface of the outer sleeve to prevent unintentional ejection of the core from the outer sleeve.

13. The medical device of claim 10, wherein the brush comprises at least one of at least one key or keyway for engaging the other of at least one keyway or key on the hollow shaft or core.

14. The medical device of claim 10, wherein the brush includes one of angled bristles or a shaft retaining the bristles that is angled or curved relative to a primary axis of the device.

15. A method of manufacturing a medical diagnostic device, the method comprising:
- providing an outer sleeve having a hollow interior and open distal and proximal ends, the outer sleeve including a proximal section having a conical shape;
- providing a core configured to be inserted axially within in the outer sleeve, the core including an axial cavity and a proximal section having a conical shape substantially conforming to the proximal section of the outer sleeve, and
- providing a diagnostic assembly within the core.

16. The method of claim 15, wherein the diagnostic assembly provided is a sample collecting assembly made from the steps of:
- providing a hollow rotatable shaft extending through the axial cavity of the core, the shaft having an engagement member positioned at a proximal end of the shaft and retained within the conical section of the core;
- providing an ejector pin extending entirely through the hollow rotatable shaft; and
- providing a sample collector coupled to the ejector pin.

17. The method of claim 15, wherein the diagnostic assembly comprises an imaging device and in which the method further comprises positioning the imaging device in a sampling end of the axial cavity of the core.

18. The method of claim 15, further comprising the step of configuring a distal expansion section of the outer sleeve to transition between an unopened insertion position and an open deployed position.

19. The method of claim 17, further comprising the step of permitting the sample collector to rotate while restricting the rotational movement of the imaging device.

* * * * *